United States Patent
Pfeffer

(10) Patent No.: US 6,664,080 B1
(45) Date of Patent: Dec. 16, 2003

(54) **TAQMAN™-PCR FOR THE DETECTION OF PATHOGENIC *E. COLI* STRAINS**

(75) Inventor: Klaus Pfeffer, Munich (DE)

(73) Assignee: Bavarian Nordic Research Institute, Copenhagen (DK)

( * ) Notice: Subject to any disclaimer, the term of this patent is extended or adjusted under 35 U.S.C. 154(b) by 0 days.

(21) Appl. No.: 09/403,690

(22) PCT Filed: Apr. 21, 1998

(86) PCT No.: PCT/EP98/02341

§ 371 (c)(1),
(2), (4) Date: Jan. 26, 2000

(87) PCT Pub. No.: WO98/48046

PCT Pub. Date: Oct. 29, 1998

(30) Foreign Application Priority Data

Apr. 22, 1997 (DK) ............................................. 0451/97

(51) Int. Cl.[7] ........................... C12P 19/34; C12Q 1/68; C07H 21/04

(52) U.S. Cl. ...................... 435/91.2; 435/6; 435/91.2; 536/24.32; 536/24.3; 536/23.1

(58) Field of Search ................ 435/6, 91.2; 536/24.32, 536/24.3, 23.1

(56) References Cited

U.S. PATENT DOCUMENTS 5,041,372 A * 8/1991 Lampel et al. ................. 435/6
5,595,874 A * 1/1997 Hogan et al. .................. 435/6

FOREIGN PATENT DOCUMENTS

| EP | 0 556 504 A | 8/1993 |
| EP | 0556504 A2 * | 8/1993 |
| EP | 0 669 399 A | 8/1995 |
| WO | 96 08582 A | 3/1996 |
| WO | 96 12801 A | 5/1996 |

OTHER PUBLICATIONS

Stacy–Phipps, Sandrina, et al., "Multiplex PCR Assay and Simple Preparation Method for Stool Specimens Detect Enterotoxigenic *Escherichia coli* DNA during Course of Infection" (May 1995) Journal of Clincial Microbiology, p. 1054–1059.
Lett et al. (Food Testing and Analysis, Dec. 1995/Jan. 1996, 34–38).*
Bassler et al. (Applied and Environmental Microbiology, Oct. 1995, vol. 61, No. 10, p. 3724–3728).*
Levine et al. American Journal of Epidemiology (1993) 138(10): 849–896.*
Paton et al. GenBank Accession No. Z36899. May 1995. Database accessed Aug. 21, 2001.*
Louie et al. Epidemiol. Infect (1994) 112:449–461.*
Mosley et al. GenBank Accession M34916. Apr. 1993. Database Accessed Aug. 21, 2001.*

Yamamoto et al. Infection and Immunology. 1996. 64(4):1441–1445.*
Franke et al. Journal of Clinical Microbiology. 1994. 32(10):2460–2463.*
Kaper. GenBank Accession Z11541. Dec. 1995. Database Accessed Aug. 21, 2001.*
Paton et al. GenBank Accession Z36899. May 1995. Database accessed Aug. 23, 2001.*
Paton et al. GenBank Accession L11079. Feb. 1994. Database accessed Aug. 21, 2001.*
Lang et al. Applied and Environmental Microbiology. 1994. 60 (9):3145–3149.*
Yamamoto et al. Journal of Applied Bacteriology. 1983. 155(2):728–733.*
Livak et al. PCR Methods and Applications. 1995. 4:357–362.*
Tsen et al. Journal of Food Protection. 1996. 59(8)795–802.*
Baudry, Bernadette et al., "A Sensitive and Specific DNA Probe to Identify Enteroaggregative *Escherichia coli*, a Recently Discovered Diarrheal Pathogen," (1990) *The Journal of Infectious Diseases*, vol. 161, pp. 1249–1251.
Levine, Myron M. et al., "A DNA Probe to Identify Enterohemorrhagic *Escherichia coli* of O157:H7 and Other Serotypes That Cause Hemorrhagic Colitis and Hemolytic Uremic Syndrome," (1987) *The Journal of Infectious Diseases*, vol. 156, No. 1, pp. 175–182.
Nataro, James P. et al., "Detection of an Adherence Factor of Enteropathogenic *Escherichia coli* with a DNA Probe," (1985) *The Journal of Infectious Diseases*, vol. 152, No. 3, pp. 560–565.
Savarino, Stephen J. et al., "Enteroaggregative *Escherichia coli* Heat–Stable Enterotoxin Is Not Restricted to Enteroaggregative *E. coli*," (1996), *The Journal of Infectious Diseases*, vol. 173, pp. 1019–1022.
Savarino, Stephen J et al., "Enteroaggregative *Escherichia coli* heat–stable enterotoxin 1 represents another subfamily of *E. coli* heat–stable toxin," (1993) *PNAS* 90:3093–3097.
Wood, Patrick K. et al., "Comparison of DNA Probes and the Sereny Test for Identification of Invasive Shigella and *Escherichia coli* Strains," (1986), *Journal of Clinical Microbiology*, vol. 24, No. 3, pp. 498–500.
Yamamoto, Tatsuo et al., "Comparison of the nucleotide sequence of enteroaggregative *Escherichia coli* heat–stable enterotoxin 1 genes among diarrhea–associated *Escherichia coli*," (1997), *FEMS Microbiology Letters*, vol. 147, pp. 89–95.

(List continued on next page.)

Primary Examiner—Gary Benzion
Assistant Examiner—Juliet C. Switzer
(74) Attorney, Agent, or Firm—Antoinette F. Konski; Bingham McCutchen LLP

(57) ABSTRACT

The present invention relates to a method for the detection of pathogenic *E. coli* in a sample comprising PCR amplification of DNA isolated from said sample using oligonucleotide primers specific for pathogenic *E. coli*.

16 Claims, No Drawings

OTHER PUBLICATIONS

Fratamico, P.M. et al. "Detection of *Escherichia coli* O157: H7 by Multiplex PCR," (1995) *Journal of Clinical Microbiology*, vol. 33, No. 8, pp. 2188–2191.

Schmidt, Herbert et al. "Development of PCR for screening of Enteroaggregative *Escherichia coli*," (1995) *Journal of Clinical Microbiology*, vol. 33, No. 3, pp. 701–705.

Tornieporth, Nadia G. et al. "Differentiation of Pathogenic *Escherichia coli* Strains in Brazilian Children by PCR," (1995) *Journal of Clinical Microbiology*, vol. 33, No. 5, pp. 1371–1374.

*Batt. "Molecular Diagnostics For Diary–Borne Pathogens," (1997) *Journal of Diary Science*; Medline Abstract XP002094257.

*Heid, C.A. et al. "Real Time Quantitative PCR," (1996) *Genome Research*, vol. 6, No. 10, pp. 986–994.

*Ibrahimi, Ibrahim et al. "A Functional Interaction Between The Signal Peptide And The Translation Apparatus Is Detected By The Use Of A Single Point Mutation Which Blocks Translocation Across Mammalian Endoplasmic Reticulum," (1987) *Journal of Biological Chemistry*, vol. 262, No. 21, pp. 10189–10194.

BLAST search performed on Jan. 14, 2002; query sequence: from Savarino et al (1993) PNAS 90:3093 (5' TAGGATC-CTCAGGTCGCGACTGACGGC 3'); databases searched: GenBank+EMBL|DDBG+PDB sequences but no EST, STS, GSS, or phase 0, 1, or 2 HGTS sequences.

* cited by examiner

SEQUENCE LISTING

```
<160> NUMBER OF SEQ ID NOS:  30

<210> SEQ ID NO 1
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 1 gcg tta cta tcc tct cta tgt g                                          22
Ala Leu Leu Ser Ser Leu Cys
 1               5

<210> SEQ ID NO 2
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 2 agt ttt cca tac tga ttg ccg c                                          22
Ser Phe Pro Tyr  *  Leu Pro
 1               5

<210> SEQ ID NO 3
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 3
```

```
tcc ctc agg atg cta aac cag                                           21
Ser Leu Arg Met Leu Asn Gln
 1               5

<210> SEQ ID NO 4
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 4 tcg att tat tca aca aag caa c                                         22
Ser Ile Tyr Ser Thr Lys Gln
 1               5

<210> SEQ ID NO 5
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 5 aac tgc tgg gta tgt ggc tgg                                           21
Asn Cys Trp Val Cys Gly Trp
 1               5

<210> SEQ ID NO 6
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 6 tgc tga cct gcc tct tcc atg                                           21
Cys  *  Pro Ala Ser Ser Met
 1               5

<210> SEQ ID NO 7
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 7 ctg gcg aaa gac tgt atc att g                                         22
Leu Ala Lys Asp Cys Ile Ile
 1               5

<210> SEQ ID NO 8
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 8 taa tgt ata gaa atc cgc tgt t                                         22
 *  Cys Ile Glu Ile Arg Cys
     1               5
```

```
<210> SEQ ID NO 9
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 9 ttt ctg gat ggt atg gtg agg                                           21
Phe Leu Asp Gly Met Val Arg
 1               5

<210> SEQ ID NO 10
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 10 ctt gaa cat aag gaa ata aac                                           21
Leu Glu His Lys Glu Ile Asn
 1               5

<210> SEQ ID NO 11
<211> LENGTH: 23
<212> TYPE: DNA
<213> ORGANISM: Escherichia coli
<220> FEATURE:
<221> NAME/KEY: CDS
<222> LOCATION: (1)...(23)

<400> SEQUENCE: 11 cag ggt aaa aga aag atg ata ag                                        23
Gln Gly Lys Arg Lys Met Ile
 1               5

<210> SEQ ID NO 12
<211> LENGTH: 22
<212> TYPE: DNA
<213> ORGANISM: Escherichia coli
<220> FEATURE:
<221> NAME/KEY: CDS
<222> LOCATION: (1)...(22)

<400> SEQUENCE: 12 aat atg ggg acc atg tat tat c                                         22
Asn Met Gly Thr Met Tyr Tyr
 1               5

<210> SEQ ID NO 13
<211> LENGTH: 23
<212> TYPE: DNA
<213> ORGANISM: Escherichia coli
<220> FEATURE:
<221> NAME/KEY: CDS
<222> LOCATION: (1)...(23)

<400> SEQUENCE: 13 ccc gca ccc ggc aca agc ata ag                                        23
Pro Ala Pro Gly Thr Ser Ile
 1               5

<210> SEQ ID NO 14
<211> LENGTH: 22
<212> TYPE: DNA
```

```
<213> ORGANISM: Escherichia coli
<220> FEATURE:
<221> NAME/KEY: CDS
<222> LOCATION: (1)...(22)

<400> SEQUENCE: 14 agt ctc gcc agt att cgc cac c                                           22
Ser Leu Ala Ser Ile Arg His
  1               5

<210> SEQ ID NO 15
<211> LENGTH: 23
<212> TYPE: DNA
<213> ORGANISM: Escherichia coli
<220> FEATURE:
<221> NAME/KEY: CDS
<222> LOCATION: (1)...(23)

<400> SEQUENCE: 15 atg aaa aca tta tta ata gc                                              23
Met Lys Lys Thr Leu Leu Ile
  1               5

<210> SEQ ID NO 16
<211> LENGTH: 24
<212> TYPE: DNA
<213> ORGANISM: Escherichia coli
<220> FEATURE:
<221> NAME/KEY: CDS
<222> LOCATION: (1)...(24)

<400> SEQUENCE: 16 tca cyg agc tat tct gag tca agc                                         24
Ser Xaa Ser Tyr Ser Glu Ser Ser
  1               5

<210> SEQ ID NO 17
<211> LENGTH: 31
<212> TYPE: DNA
<213> ORGANISM: Escherichia coli
<220> FEATURE:
<221> NAME/KEY: CDS
<222> LOCATION: (1)...(31)

<400> SEQUENCE: 17 atg aag aag atr wtt rtd gcr gyt tta tty g                               31
Met Lys Lys Xaa Xaa Xaa Xaa Xaa Leu Phe
  1               5                  10

<210> SEQ ID NO 18
<211> LENGTH: 33
<212> TYPE: DNA
<213> ORGANISM: Escherichia coli
<220> FEATURE:
<221> NAME/KEY: CDS
<222> LOCATION: (1)...(33)

<400> SEQUENCE: 18 tca gtc atw att aaa ctk cac yts rgc aaa kcc                             33
Ser Val Xaa Ile Lys Xaa His Xaa Xaa Lys Xaa
  1               5                  10

<210> SEQ ID NO 19
<211> LENGTH: 27
<212> TYPE: DNA
<213> ORGANISM: Escherichia coli
<220> FEATURE:
<221> NAME/KEY: CDS
<222> LOCATION: (1)...(27)
```

-continued

```
<400> SEQUENCE: 19 agc tcc cca gtc tat tac aga act atg                              27
Ser Ser Pro Val Tyr Tyr Arg Thr Met
 1               5

<210> SEQ ID NO 20
<211> LENGTH: 29
<212> TYPE: DNA
<213> ORGANISM: Escherichia coli
<220> FEATURE:
<221> NAME/KEY: CDS
<222> LOCATION: (1)...(29)

<400> SEQUENCE: 20 aca tac gtt aca gac ata atc aga atc ag                           29
Thr Tyr Val Thr Asp Ile Ile Arg Ile
 1               5

<210> SEQ ID NO 21
<211> LENGTH: 30
<212> TYPE: DNA
<213> ORGANISM: Escherichia coli
<220> FEATURE:
<221> NAME/KEY: CDS
<222> LOCATION: (1)...(30)

<400> SEQUENCE: 21 atg aag ggg cga agt tct ggc tca atg tgc                          30
Met Lys Gly Arg Ser Ser Gly Ser Met Cys
 1               5                  10

<210> SEQ ID NO 22
<211> LENGTH: 30
<212> TYPE: DNA
<213> ORGANISM: Escherichia coli
<220> FEATURE:
<221> NAME/KEY: CDS
<222> LOCATION: (1)...(30)

<400> SEQUENCE: 22 ctc ttt taa ctt atg ata tgt aat gtc tgg                          30
Leu Phe  *  Leu Met Ile Cys Asn Val Trp
 1               5

<210> SEQ ID NO 23
<211> LENGTH: 27
<212> TYPE: DNA
<213> ORGANISM: Escherichia coli
<220> FEATURE:
<221> NAME/KEY: CDS
<222> LOCATION: (1)...(27)

<400> SEQUENCE: 23 caa aaa cag aag aac cta tgt cta cct                              27
Gln Lys Gln Lys Asn Leu Cys Leu Pro
 1               5

<210> SEQ ID NO 24
<211> LENGTH: 27
<212> TYPE: DNA
<213> ORGANISM: Escherichia coli
<220> FEATURE:
<221> NAME/KEY: CDS
<222> LOCATION: (1)...(27)

<400> SEQUENCE: 24 ctt gga gtg atc gaa cgg gat cca aat                              27
```

```
Leu Gly Val Ile Glu Arg Asp Pro Asn
  1               5
```

<210> SEQ ID NO 25
<211> LENGTH: 28
<212> TYPE: DNA
<213> ORGANISM: Escherichia coli
<220> FEATURE:
<221> NAME/KEY: CDS
<222> LOCATION: (1)...(28)

<400> SEQUENCE: 25

```
taa acg ggt att atc aac aga aaa atc c                              28
 *  Thr Gly Ile Ile Asn Arg Lys Ile
        1               5
```

<210> SEQ ID NO 26
<211> LENGTH: 30
<212> TYPE: DNA
<213> ORGANISM: Escherichia coli
<220> FEATURE:
<221> NAME/KEY: CDS
<222> LOCATION: (1)...(30)

<400> SEQUENCE: 26

```
tcg ctg aat ccc cct cca tta tga cag gca                            30
Ser Leu Asn Pro Pro Pro Leu  *  Gln Ala
  1               5
```

<210> SEQ ID NO 27
<211> LENGTH: 30
<212> TYPE: DNA
<213> ORGANISM: Escherichia coli
<220> FEATURE:
<221> NAME/KEY: CDS
<222> LOCATION: (1)...(30)

<400> SEQUENCE: 27

```
cag gta ctg gat ttg att gtg aca gtc att                            30
Gln Val Leu Asp Leu Ile Val Thr Val Ile
  1               5                  10
```

<210> SEQ ID NO 28
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 28

```
aac ctg ttc agc gcc gca ttg                                        21
Asn Leu Phe Ser Ala Ala Leu
  1               5
```

<210> SEQ ID NO 29
<211> LENGTH: 21
<212> TYPE: DNA
<213> ORGANISM: Escherichia coli
<220> FEATURE:
<221> NAME/KEY: CDS
<222> LOCATION: (1)...(21)

<400> SEQUENCE: 29

```
aca acc ggg att cgg tgt aac                                        21
Thr Thr Gly Ile Arg Cys Asn
  1               5
```

-continued

```
<210> SEQ ID NO 30
<211> LENGTH: 30
<212> TYPE: DNA
<213> ORGANISM: Escherichia coli
<220> FEATURE:
<221> NAME/KEY: CDS
<222> LOCATION: (1)...(30)

<400> SEQUENCE: 30 atg tct gaa ctg ggc ctg aat gcc agc gcc                         30
Met Ser Glu Leu Gly Leu Asn Ala Ser Ala
1               5                   10
```

TAQMAN™-PCR FOR THE DETECTION OF PATHOGENIC *E. COLI* STRAINS

The present invention relates to a rapid, high performance assay for the detection of pathogenic *E. coli* which is based on TaqMan™ PCR technique, and to specific optimised oligonucleotide primers and labelled oligonucleotide probes useful in the assay.

BACKGROUND OF THE INVENTION

Enterohemorrhagic, shiga-like toxin (slt) producing *Escherichia coli* (EHEC) have recently been recognized as an important human and animal pathogen (1–7). EHEC has been responsible for several food-borne outbreaks (8). The most notable were a multistate outbreak associated with a fast food chain in the western states of the USA with more than 600 individuals affected and 3 deaths in Washington (9), and an epedemic occurence in Japan with more than 6000 patients and approx. 8 fatal cases (10). Infection with EHEC causes diarrhea, hemorrhagic colitis, thrombotic thrombocytopenic purpura, and hemolytic uremic syndrome (HUS) that is characterised by acute renal failure, thrombocytopenia, and microangiopathic hemolytic anemia. HUS ultimately can result in a fatal outcome in affected children and immunocompromised individuals (3,11–17). Recently, in the South-Eastern parts of Germany (Bavaria) an increase of EHEC cases was reported during October 1995 and July 1996 with at least 45 severe infections leading to HUS accompanied by 7 deaths (18). Estimating that approx. 1 out of 15 EHEC infections results in HUS approx. 600–700 affected individuals might be assumed.

In most outbreaks reported, consumption of contaminated ground beef has been the source of infection (5,8,19–22), whereas in Japan raddish sprouts are suspected (10). EHEC has been isolated from cow milk (6,19,23), water (19), chicken, pork, and apple cider (19,24,25), but also human horizontal smear infections have been reported (15). Cattle appear likely to be the reservoir (22,26). Cross contamination, improper handling, and inadequate cooking all contribute to food-borne infections caused by EHEC. EHEC produce Shiga-like toxins (slt), also known as verotoxins or cytotoxins (12,27). A large proportion of EHEC have been found to belong to the serogroup O157:H7, but notably, also a variety of EHEC belonging to other serogroups (O22, O26, O55, O111, O114, O145) have been reported especially in Europe (12,15,28–32).

Besides EHEC, certain other strains of *E. coli* can cause enteritis or gastroenteritis and are grouped in enterotoxigenic strains (ETEC) (33–36), enteropathogenic strains (EPEC) (37), enteroinvasive strains (EIEC) (38,39), and enteroaggregative strains (EaggEC) (40,41). These strains are important pathogens and also pose severe public health problems. The diagnosis of these pathogens is vastly neglegted due to the lack of specific and sensitive routine test methods. ETEC synthesize heat labile and/or heat stable enterotoxins that can cause a secretory diarrhea ("traveller's diarrhea") resembling that of *Vibrio cholerae* (36,42,43). Surface attachment of the ETEC organisms to the intestinal epithelial cell is a prerequisite to toxin production. Toxin production is plasmid mediated and most commonly involves *E. coli* serogroups O6, O15, O124, O136, O143, O145, and 0147 (32). EPEC cause diarrheal symptoms primarily in infants (32). Although the pathogenesis is unclear, the epithelial degradation of the gut, and the inflammatory response that are observed in tissue sections may be a consequence due to the adhesive properties of the bacterium. Specific attachment factors of EPEC are plasmid encoded (EAF=EPEC adherence factor) (37,44). EHEC often contain an adherence factor closely related to EAF that is known as ene (EHEC attaching and effacing gene) (45, 46). EPEC most often belong to serogroups O6, O8, O25, O111, O119, and O142 (32).

EIEC strains are capable of penetrating and invading the intestinal epithelial cells and produce an inflammatory diarrhea similar to that caused by Shigella bacteria (38,47,48). Fecal smears contain blood, mucus and segmented neutrophils. EIEC contain virulence plasmids coding for additional pathogenic factors (48). Serogroups O28, O112, O115, O124, O136, O143, O145, and O147 are most commonly found on EIEC (32).

EaggEC are associated with persistent diarrhea in children and with traveller's diarrhea. EaggEC are characterized by their adherence capacity that leads to aggregation of Hep-2 cells. This effect is associated with the presence of a virulence plasmid (pCVD432). EaggEC are supected to also produce a heat stable enterotoxin (EAST1) (49–53). They can belong to serogroups O44 and O126 (32).

Conventional detection methods for EHEC encompass enrichment and isolation with selective and/or indicator media such as *E. coli* broth, lauryl sulfate tryptose 4-methylumbelliferyl-b-acid broth, eosin methylene blue agar, McConkey sorbitol agar, and enterohemolysin agar (28,32,54–59). All of these assays, unfortunately, are indirect and lack the ability to identify EHEC or the other pathogenic *E. coli* strains specifically. Several methods for biochemical identification and immunological detection of EHEC have been put forward (54,60–63), however, it is well recognized that pathogenic *E. coli* strains neither posess nor lack unique fermentation pathways (58,64). Serotyping is not conclusive since no absolute correlation between serotype and pathogenic *E. coli* group can be established (12, 27,32,58,65). DNA hybridization techniques have been established for experimental research but are not applicable for large scale routine diagnostic procedures (66,67). DNA amplification based assays, using PCR have been reported (68–72). Limitations to these methods include cumbersome post-PCR detection methods (agarose gel electrophoresis, Biotin/Avidin based ELISA detection systems).

To overcome these problems, a PCR assay which allows the specific determination of virulence factors characteristic for EHEC, ETEC, EPEC, EIEC, and EaggEC that is based on a fluorigenic detection method of PCR amplification has been developed.

This assay exploits the 5'→3' exonuclease activity of Taq-DNA polymerase (73) to cleave an internal oligonucleotide probe that is covalently conjugated with a fluorescent reporter dye (e.g. 6-carboxy-fluorescein [FAM]; $\lambda_{em}$=518 nm) and a fluorescent quencher dye (6-carboxytetram-ethylrhodamine [TAMRA]; $\lambda_{em}$=582 nm) at the 5' and 3' end, respectively (74,75). Fluorescence from FAM is efficiently quenched by TAMRA on the same, intact probe molecule (76). In the case that cognate PCR amplification occurs, Taq polymerase extends from the specific PCR primer and cleaves the internal, fluorigenic oligonucleotide probe annealed to the template strand. Thus, the reporter dye and the quencher dye get spatially separated. As a consequence of oligonucleotide hydrolysis and physical separation of the reporter and the quencher dyes, a measurable increase in fluoresecence intensity at 518 nm can be observed. PCR cycling leads to exponential amplification of the PCR product and consequently of fluorescence intensity.

TAQMAN™-PCR is performed in optical tubes that allow measurements of fluorescence signals without opening the PCR tubes. This dramatically minimizes post-PCR processing time and almost completely eliminates cross-PCR contamination problems. Employing this approach, simultaneous testing of biological materials for the presence of virulence genes of Lcoh strains and other enterobacteria, harboring virulence genes can be semiautomated and performed within 18 h.

According to the present invention Real Time PCR (e.g., TAQMAN™ PCR) for the detection of pathogenic *E. coli* is provided, enabling for the first time the specific, rapid and high throughput routine detection of EHEC, ETEC, EPEC, EIEC, and EaggEC and related enterobacteria that harbor these virulence genes in routine bacteriological laboratories.

OBJECT OF THE INVENTION

It is an object of the present invention to provide a rapid, high performance assay for the detection and identification of pathogenic *E. coli* in biological samples.

It is a further object of the present invention to provide specific, optimised primers and labelled oligonucleotide probes useful for the amplification of sequences encoding virulence factors/toxins characteristic for pathogenic *E. coli*

SUMMARY OF THE INVENTION

The invention then, inter alia, comprises the following alone or in combination:

A method for the detection of pathogenic *E. coli* in a sample comprising PCR amplification of DNA isolated from said sample using a set of oligonucleotide primers specific for virulence factors/toxins of pathogenic *E. coli* selected from primers that hybridise to a gene encoding heat labile toxin, or heat stabile toxin for the amplification of a DNA sequence characteristic for enterotoxigenic *E. coli*;

primers that hybridise to a gene encoding heat stabile toxin for the amplification of a DNA sequence characteristic for enteroaggregative *E. coli*;

primers that hybridise to the pCVD432 plasmid for the amplification of a DNA sequence characteristic for enteroaggregative *E. coli*;

primers that hybridise to the inv-plasmid for the amplification of a DNA sequence contained in enteroinvasive *E. coli*;

primers that hybridise to the EAF plasmid, or the eae gene for the amplification of a DNA sequence characteristic for enteropathogenic *E. coli*; and/ or primers that hybridise to the genes encoding shiga-like toxin sltI or sltII for the amplification of a DNA sequence characteristic for enterohemorrhagic *E. coli*, followed by detection and identification of the amplified product using conventional methods;

the method as above wherein the set of primers that hybridise to the gene encoding heat labile toxin characteristic for enterotoxigenic *E. coli* is LT-1: $^{5'}$GCG TTA CTA TCC TCT CTA TGT G$^{3'}$ (SEQ ID NO:1) and

LT-2: $^{5'}$AGT TTT CCA TAC TGA TTG CCG C$^{3'}$ (SEQ ID NO:2);

the set of primers that hybridise to the gene encoding heat stabile toxin characteristic for enterotoxigenic *E. coli* is ST-1: $^{5'}$TCC CTC AGG ATG CTA AAC CAG$^{3'}$ (SEQ ID NO:3) and ST-2a: $^{5'}$TCG ATT TAT TCA ACA AAG CAA C$^{3'}$ (SEQ ID NO:4);

the set of primers that hybridise for the gene encoding heat stabile toxin characteristic for enteroaggregative *E. coli* is EASTI-1: $^{5'}$AAC TGC TGG GTA TGT GGC TGG$^{3'}$ (SEQ ID NO:5) and

EASTI-2: $^{5'}$TGC TGA CCT GCC TCT TCC ATC$^{3'}$ (SEQ ID NO:6);

the set of primers which hybridise to the pCVD432 plasmid is

EA-1: $^{5'}$CTG GCG AAA GAC TGT ATC ATT G$^{3'}$ (SEQ ID NO:7) and

EA-2: $^{5'}$TAA TGT ATA GAA ATC CGC TGT T$^{3'}$ (SEQ ID NO:8);

the set of primers which hybridise to the inv-plasmid is

EI-1: $^{5'}$TTT CTG GAT GGT ATG GTG AGG$^{3'}$ (SEQ ID NO:9) and

EI-2: $^{5'}$CTT GAA CAT AAG GAA ATA AAC$^{3'}$ (SEQ ID NO:10);

the set of primers which hybridise to the EAF plasmid is

EP-1: $^{5'}$CAG GGT AAA AGA AAG ATG ATA AG$^{3'}$ (SEQ ID NO:11) and

EP-2: $^{5'}$AAT ATG GGG ACC ATG TAT TAT C$^{3'}$ (SEQ ID NO:12)

the set of primers which hybridise to the eae gene is

EPeh-1: $^{5'}$CCC GGA CCC GGC ACA AGC ATA AG$^{3'}$ (SEQ ID NO:13) and

EPeh-2: $^{5'}$AGT CTC GCC AGT ATT CGC CAC C$^{3'}$ (SEQ ID NO:14);

the primers which hybridises to the gene encoding shiga-like toxin SltI is

SltI-1: $^{5'}$ATG AAA AAA ACA TTA TTA ATA GC$^{3'}$ (SEQ ID NO:15) and

SltI-2: $^{5'}$TCA CYG AGC TAT TCT GAG TCA AGC$^{3'}$ (SEQ ID NO:16); and the primers which hybridises to the gene encoding shiga-like toxin SltII is SltII-1: $^{5'}$ATG AAG AAG ATR WTT RTD GCR GYT TTA TTY G$^{3'}$ (SEQ ID NO:17) and SltII-2: $^{5'}$TCA GTC ATW ATT AAA CTK CAC YTS RGC AAA KCC$^{3'}$ (SEQ ID NO:18)

wherein W is A/T, R is A/G, D is A/G/T, Y is C/T and K is G/T; the method as above wherein a polymerase having additional 5'-3' exonuclease activity is used for the amplification of DNA, and an oligonucleotide probe labelled at the most 5' base with a fluorescent dye and at the most 3' base with a fluorescent quencher dye which hybridises within the target DNA is included in the amplification process; said labelled oligonucleotide probe being susceptible to 5'-3' exonuclease degradation by said polymerase to produce fragments that can be detected by fluorogenic detection methods;

the method as above wherein the labelled oligonucleotide probe for the detection of heat labile toxin characteristic for enterotoxigenic *E. coli*

5'AGC TCC CCA GTC TAT TAC AGA ACT ATG³' (SEQ ID NO:19);

the labelled oligonucleotide probe for the detection of heat stabile toxin characteristic for enterotoxigenic *E. coli* is
5'ACA TAC GTT ACA GAC ATA ATC AGA ATC AG³' (SEQ ID NO:20);
the labelled oligonucleotide probe for the detection of heat stabile toxin characteristic for enteroaggregative *E. coli* is

5'ATG AAG GGG CGA AGT TCT GGC TCA ATG TGC³' (SEQ ID NO:21);

the labelled oligonucleotide probe for the detection of pCVD432 plasmid is

5'CTC TTT TAA CTT ATG ATA TGT AAT GTC TGG³' (SEQ ID NO:22);

the labelled oligonucleotide probe for the detection of the inv-plasmid is;

5'CAA AAA CAG AAG AAC CTA TGT CTA CCT³' (SEQ ID NO:23)

the labelled oligonucleotide probe for the detection of the EAF-plasmid is;

5'CTT GGA GTG ATC GAA CGG GAT CCA AAT³' (SEQ ID NO:24);

the labelled oligonucleotide probe for the detection of the eae gene is

5'TAA ACG GGT ATT ATC AAC AGA AAA ATC C³' (SEQ ID NO:25);

the labelled oligonucleotide probe for the detection of shiga-like toxin SltI gene is 5'TCG CTG AAT CCC CCT CCA TTA TGA CAG GCA³' (SEQ ID NO:26); and the labelled oligonucleotide probe for the detection of shiga-like toxin SltII gene is

5'CAG GTA CTG GAT TTG ATT GTG ACA GTC ATT³' (SEQ ID NO:27);

the method as above wherein the fluoroscent reporter dye is 6-carboxy-fluoroscein, tetrachloro-6-carboxy-fluoroscein, or hexachloro-6-carboxy-fluoroscein, and the fluorescent quencher dye is 6-carboxytetramethyl-rhodamine;

the method as above wherein the PCR amplification process consists of 35 PCR cycles at a $MgCl_2$ concentration of 5.2 mmol, an annealing temperature of 55° C. and an extension temperature of 65° C.;

a set of primers useful for PCR amplification of DNA specific for virulence factors/toxins of pathogenic *E. coli* selected from:

a set of primers that hybridise to a gene encoding heat labile toxin, or heat stabile toxin of enterotoxigenic *E. coli;* a set of primers that hybridise to a gene encoding heat stabile toxin of enteroaggregative *E. coli;* a set of primers that hybridise to the pCVD432 plasmid of enteroaggregative *E. coli;* a set of primers that hybridise to the inv-plasmid of enteroinvasive *E. coli;* a set of primers that hybridise to the EAF plasmid, or the eae gene of enteropathogenic *E. coli;* and a set of primers that hybridise to the gene encoding shiga-like toxin sltI or sltII of enterohemorrhagic *E. coli;* the set of primers as above wherein the set of primers which hybridise to the gene encoding heat labile toxin of enterotoxigenic *E. coli* is LT-1: 5'GCG TTA CTA TCC TCT CTA TGT G³' (SEQ ID NO:1) and LT-2: 5'AGT TTT CCA TAC TGA TTG CCG C³' (SEQ ID NO:2);

the set of primers which hybridise to the gene encoding heat stabile toxin of enterotoxigenic *E. coli* is ST-1: 5'TCC CTC AGG ATG CTA AAC CAG³' (SEQ ID NO:3) and
ST-2a: 5'TCG ATT TAT TCA ACA AAG CAA C³' (SEQ ID NO:4);

the set of primers which hybridise to the gene encoding heat stabile toxin of enteroaggregative *E. coli* is EASTI-1: 5'AAC TGC TGG GTA TGT GGC TGG³' (SEQ ID NO:5) and
EASTI-2: 5'TGC TGA CCT GCC TCT TCC ATG³' (SEQ ID NO:6);

the set of primers which hybridise to the pCVD432 plasmid is

EA-1: 5'CTG GCG AAA GAC TGT ATC ATT G³' (SEQ ID NO:7) and
EA-2: 5'TAA TGT ATA GAA ATC CGC TGT T³' (SEQ ID NO:8);

the set of primers which hybridise to the inv-plasmid is

EI-1: 5'TTT CTG GAT GGT ATG GTG AGG³' (SEQ ID NO:9) and
EI-2: 5'CTT GAA CAT AAG GAA ATA AAC³' (SEQ ID NO:10);

the set of primers which hybridise to the EAF plasmid is

EP-1: 5'CAG GGT AAA AGA AAG ATG ATA AG³' (SEQ ID NO:11) and
EP-2: 5'AAT ATG GGG ACC ATG TAT TAT C³' (SEQ ID NO:12);

the set of primers which hybridise to the eae gene is

EPeh-1: 5'CCC GGA CCC GGC ACA AGC ATA AG³' (SEQ ID NO:13) and
EPeh-2: 5'AGT CTC GCC AGT ATT CGC CAC C³' (SEQ ID NO:14);

the set of primers which hybridise to the shiga-like toxin sltI gene is

SltI-1: 5'ATG AAA AAA ACA TTA TTA ATA GC³' (SEQ ID NO:15) and
SltI-2: 5'TCA CYG AGC TAT TCT GAG TCA AGC³' (SEQ ID NO:16);

and
the set of primers which hybridise to the shiga-like toxin sltII is

SltI-1: 5'ATG AAG AAG ATR WTT RTD GCR GYT TTA TTY G3' (SEQ ID NO:17) and
SltII-2: 5'TCA GTC ATW ATT AAA CTK CAC YTS RGC AAA KCC3' (SEQ ID NO:18)

wherein W is A/T, R is A/G, D is A/G/T, Y is C/T and K is G/T;

the set of primers as above which in addition to the primers for amplification of target DNA comprise a labelled oligonucleotide probe which is labelled with a fluorescent reporter dye, such as 6-carboxy-fluoroscein, tetrachloro-6-carboxy-fluoroscein, hexachloro-6-carboxy-fluoroscein, at the most 5' base and a fluorescent quencher dye, such as 6-carboxytetramethyl-rhodamine, at the most 3' base, and have a nucleotide sequence selected from

5'AGC TCC CCA GTC TAT TAC AGA ACT ATG3' (SEQ ID NO:19)

which hybridises to a gene encoding heat labile toxin of enterotoxigenic *E. coli*;

5'ACA TAC GTT ACA GAC ATA ATC AGA ATC AG3' (SEQ ID NO:20)

which hybridises to a gene encoding heat stabile toxin of enterotoxigenic *E. coli*;

5'ATG AAG GGG CGA AGT TCT GGC TCA ATG TGC3' (SEQ ID NO:21)

which hybridises to a gene encoding heat stabile toxin of enteroaggregative *E. coli*;

5'CTC TTT TAA CTT ATG ATA TGT AAT GTC TGG3' (SEQ ID NO:22)

which hybridises to the pCVD432 plasmid;

5'CAA AAA CAG AAG AAC CTA TGT CTA CCT3' (SEQ ID NO:23)

which hybridises to the inv-plasmid;

5'CTT GGA GTG ATC GAA CGG GAT CCA AAT3' (SEQ ID NO:24)

which hybridises to the EAF plasmid;

5'TAA ACG GGT ATT ATC AAC AGA AAA ATC C3' (SEQ ID NO:25)

which hybridises to the eae gene;

5'TCG CTG AAT CCC CCT CCA TTA TGA CAG GCA3' (SEQ ID NO:26)

which hybridises to the shiga-like toxin SltI gene; and

5'CAG GTA CTG GAT TTG ATT GTG ACA GTC ATT3' (SEQ ID NO:27)

which hybridises to the shiga-like toxin SltII gene;
the use of the method as above for diagnosing an *E. coli* infection of a living animal body, including a human, or for the detection of *E. coli* contamination of consumables, such as meat, milk and vegetables.

The Invention

Conventional methods used to detect PCR amplification are laboursome, employ potentially carcinogenic substances (ethidium bromide gel electrophoresis), and are not suited as a routine assay method in the microbiological routine laboratory (68–72). This poses a serious problem, especially when potential pathogenic bacteria cannot be differentiated from facultative pathogenic or apathogenic ones due to characteristic biochemical, serological and/or morphological criteria. Thus, specific nucleic acid-based diagnostic methods that directly detect virulence factors or toxins harbored by these species are mandatory. This is in principal the case for the diagnosis of pathogenic *E. coli* bacteria. Biochemical properties of EHEC, EPEC, EIEC, ETEC, and EaggEC are not unique and cannot be used for setting them apart from other *E. coli* strains (54,60–62). Furthermore, virulence plasmids of *E. coli* can be found in other enterobacteria as well (38,48,83,88,89). Because of the diverse serological makeup, identification of pathogenic *E. coli* by serotyping is also not an accurate means of identification (12,15,28–32). Classical colony hybridization assays with probes specific for characteristic virulence factor and/or toxin genes are laborous and timeconsuming (66,67). Classical PCR methods require various post-PCR steps in order to verify whether specific amplification of a target gene has occured (68J2). The TAQMAN™-PCR detection system (74,75,90) enables the rapid, specific, sensitive, and high-throughput diagnosis for differentiation of pathogenic Lcoli strains from other strains of *E. coli*. The assay has the ability to quantify the initial target sequence. Since PCR-reaction tubes have not to be opened after PCR cycling, the potential danger of cross-PCR contamination is almost negligible. The scanning time of 96 samples is approximately 8 min, and calculation of test results can be automated with a commercially available spread sheet program. Thus, overall post-PCR processing time is cut to a minimum.

The TAQMAN™-System relies on standard PCR technique with the addition of a specific internal fluorogenic oligonucleotide probe. The combination of conventional PCR with the Taq polymerase-dependent degradation of an internally hybridized ohgonucleotide probe confers also specificity to this detection method, since it is highly unlikely that unspecific PCR amplification will yield positive fluorescence signals. Some rules for chosing the fluorigenic probes have to be obeyed (74,75). Criticial are the lenght of the probe, the location of reporter and quencher dyes and the absence of a guanosine at the 5'-end (74). Also, the distance of the probe from one of the specific PCR primers is important. This is due to the fact that the probe has to stay annealed to the template strand in order to be cleaved by Taq polymerase. Since annealing depends, at least partially, on the Tm of the probe, probes should be designed to have a higher Tm as the primers. According to the present invention this was solved (except for sltII) by designing probes that were 3 to 6 bp longer than the specific primers. PCR amplification includes extension of the target sequence after annealing of the primers and the Tm of the extended primers increases. For the fluorogenic oligonucleotide probe, where the 3'- end is capped in order to avoid elongation, the Tm remains constant, making it more likely that the probe dissociates before degradation by Taq polymerase. Oligonucleotide probe degradation can be optimized by spatial proximity of the fluorogenic probe and the primer. By moving the probe for SltI from 121 bp to 9 bp close to the primer, a significant improvement in ARQ values could be obtained. A second strategy of optimization of TAQMAN™-PCR is to perform PCR elongation at 65° C., where it is also less likely that the probe dissociates from the template strand before Taq polymerase reaches and hydrolizes it. Values for ΔRQ can thus again be increased about 1.2 to 1.5 fold. The increase of ΔRQ values might be due to the ratio of annealed oligonucleotide probe reached by Taq polymerase or to an increased processivity of Taq polymerase.

The concentration of fluorogenic probes influences the accuracy of TAQMAN™-results. When the probe concentrations were >50 pmol/PCR reaction only a relatively small fraction was hydrolysed by Taq polymerase. The ratio of undegraded probe to degraded probe remains high and the fluorescence emmission of the unquenched reporter dye does not significantly increase in relation to the fluorescence intensity of the reporter dye sill close to the quencher. Thus, at high probe concentrations, ARQ values are lower than with intermediate probe concentrations (10 20 pmol). When the probe concentration is too low, ΔRQ values are increased, however, variability of PCR results is increased, since probably small errors in pipeting or minimal differences between PCR reactions become critical. Optimal probe concentration that yielded smallest variabilties and highest RQ values were found at a probe concentration of 20 pmol.

Since TAQMAN™-PCR uses an internal oligonucleotide probe for detection of template amplification, specific primers and probes can be amply designed. The design of primer and probe sequences is especially important, when nucleotide sequence variants of a given gene exist. This is the case for sltI and sltII. For sltI, all published sequences were aligned and primers and probes were designed to bind to conserved regions of all three variants. For sltII, only one region of the published genes was conserved, thus this region was chosen for the fluorogenic oligonucleotide probe. The primers for amplification of sltII were designed to contain all possible nucleotide sequences at the ambiguous positions of the published sltll variants (degenerate primer approach) (79–83). By employing degenerate primers, it is possible to detect all published variants in one single PCR reaction.

The isolation method for template DNA affects the performance of the PCR. Two methods, that are suited as rapid purification steps for routine applications, namely boiling prep or spin prep were compared. Boiling preps may still contain some bacterial components that can affect PCR reactions, however, it is extremely fast. The spin prep method involves isolation steps that serve to purify DNA from potentially negatively influencing materials. ΔRQ values and sensitivity of TAQMAN™-PCR for virulence genes from enterobacteria was not found significantly increased as compared to boiling preps when template DNA was prepared by spin prep method. The overall sensitivity of TAQMAN™-PCR for all primer/probe combinations was comparable to visual scoring of PCR products by detection with ethidium bromide stained agarose gel electrophoresis. Under optimized. conditions, as few as $10^3$ cfu sltI+EHEC could be detected among $10^7$ non-pathogenic E. coli per PCR reaction.

The use of immunomagnetic detection methods for E. coli O157 (54,91) has been put forward as a means to improve sensitivity of EHEC diagnostics by enrichment of this serogroup since the first sit producing strains were found to be O157:H7 positive (1,2). However, it is obvious that EHEC that are O157 antigen negative will be missed by this method. It became clear during serotyping studies of recent EHEC isolates that the number of O157+EHEC now is small as compared to non-O157 EHEC (12,15,28,29,31). In a recent study, conducted in Southern Germany only 2 of 13 isolates were O157 positive (92). Immunomagnetic detection methods for other O serotypes are currently not available. Also, other enterobacteria such as Citrobacter sp. (83) and Enterobacter sp. (89) that can harbor shiga like toxins would be missed in the case of biased enrichment procedures previous to analysis of virulence genes. Thus, TaqMan™-based PCR that is designed for detection of virulence genes in all enterobacteria appears to be superior.

The infectious agents of a large proportion of diarrheal diseases is not known. Routine screening for bacterial pathogens in the gastrointestinal tract encompasses Salmonella sp, Shigella sp, S. aureus, Campylobacter sp., Vibrio sp., Yersinia sp., and C. difficile (32). It is well recognized that pathogenic E. coli such as ETEC, EHEC, EIEC, and EaggEC are important pathogens of the lower gastrointestinal tract and therefore might significantly contribute to the number of diarrheal infections (32). However, no routine bacteriological diagnostic procedures for these bacteria are performed, and, moreover, in most cases these pathogenic E. coli are misdiagnosed under the category of non-pathogenic "commensal flora". In order to address this problem a set of specific primers and fluorogenic probes were developed and optimized for TAQMAN™-based detection of virulence factors harbored by these bacteria (Tables 2 and 3). Arranging patient samples, positive and no-template controls of all 8 tested virulence genes in a standard 96 well microtiter format, a turnaround time from preparation of sample DNA to fluorescence measurement of under 5 hours can be achieved. Thus, the TAQMAN™-based assay for pathogenic E. coli provides an ultrarapid means of diagnosis of these bacteria. While being accurate, sensitive and specific, this assay requires minimal post PCR processing time compared to conventional methods. When TAQMAN™-PCR is performed in optical tubes also the danger of cross-contamination of PCR reactions with amplified products is reduced to a minimum. Detection of virulence plasmids harbored by pathogenic enterobacteria might prove the potential of these bacteria to cause disease in the host. It is not clear whether enterobacteria that contain toxin genes or attachment factors do also always express them outside the host. This might be an explanation why ELISA tests for shiga like toxins might be negative in a number of HUS cases where sltI and/or sltII containing EHECs can be detected by nucleic acid based methods.

The TAQMAN™-assay according to the invention for detection of pathogenic E. coli was then tested in a routine diagnostic setting for the examination of stool samples obtained from children with diarrhea within a defined geographic area (Southern Bavaria) during a 7 month period. Results obtained by TAQMAN™-PCR were compared to the standard detection method for PCR products (electrophoresis of ethidium stained agarose gels). 100 stool samples were analysed (Table 4). 22% of samples were found to test positive for one or more virulence factors. There were 2 cases. of EHEC, 5 ETEC, 8 EaggEC, 1 EIEC, and 16 EPEC. This means that ⅕ of children with diarrhea probably suffered from diarrhea caused by pathogenic E. coli. These numbers are far higher than these for all other groups of routinely screened bacterial gastrointestinal tract pathogens. Only 2 cases of salmonella and no campylobacter were observed within this group.

Interestingly, the two children diagnosed with EHEC were severely sick, one suffered from hemorrhagic colitis, the other developed HUS and had to be treated in a critical care unit.

Collectively, these investigations show that a large proportion of diarrheal diseases in children and also in adults are associated with pathogenic *E. coli* that are falsely diagnosed as commensal flora in standard microbiological procedures. The TAQMAN™ methodology according to the invention for the first time enables the direct, fast, specific, and sensitive detection of these important pathogens. Moreover, virulence genes detected with this approach are not confined to *E. coli*, they also can be freely transmitted to other enterobacteria. Detection of the virulence genes within these bacteria would also be covered by the herein described TAQMAN™-PCR The assay requires only minimal post-PCR detection time, can thus be performed under 18 hours, and abolishes PCR-cross contamination problems.

According to the present invention *E. coli* virulence factor/toxin genes were used as targets for PCR amplification. PCR primers and fluorogenic probes were designed on the basis of published sequences. Eight different primer and probe sets for detection of pathogenic groups of *E. coli* and related enterobacteria were specifically chosen, see table 1.

Primer sequences and their locations with GenBank accessions are detailed in Table 2. Detection of EHEC sltI is based on consensus primer and probe sequences after alignment of sltI homologous genes (Genbank accessions Z36899, Z36900, and Z36901) (77,78). Detection of sltII variants is based on published sequences of homologous genes (Genbank accessions M76738, Z37725, L11079, X67515, M59432, M29153, M36727, and M21534) (79–83). For amplification of sltII, degenerate primer sets proved optimal. Diagnosis of ETEC is based on amplification of either heat labile (LT) (84) or heat stable toxin (ST) (36), EaggEC on pCVD432 plasmid sequences (40,50), EIEC on inv-plasmid sequences (38,48), EPEC on *E. coli* attaching and effacing gene (EAF plasmid) (37,85) or *E. coli* gene for EHEC attaching and effacing protein (eae) (86). PCR control amplification for integrity of DNA preparations was performed using primers specific for the *E. coli* parC gene (topoisomerase IV, Genbank accession M58408) (87).

Oligonucleotide probes and their Genbank Ref. are shown in table 3. Oligonucleotide probes were designed (if possible) with a GC-content of 40–60%, no G-nucleotide at the 5'-end, length of probes was 27 to 30 bp. Probes were covalently conjugated with a fluorescent reporter dye (e.g. 6-carboxy-fluorescein [FAM]; $\lambda_{em}$=518 nm) and a fluorescent quencher dye (6-carboxytetram-ethyl-rhodamine [TAMRA]; $\lambda_{em}$=582 nm) at the most 5' and most 3' base, respectively. All primers and probes were obtained from Perkin Elmer, Germany.

TAQMAN™-PCR was optimized by isolation of DNA from *E. coli* control strains harboring genes for LT, ST, inv-plasmid, pCVD342, EAF, eae, sltI and sltII (see Table 1). MgCl$_2$ concentrations were adjusted for maximum PCR. product yields (as verified by agarose gel electrophoresis) and RQ values (RQ=FAM$_{fluorescence\ intensity}$/TAMRA$_{fluorescence\ intensity}$) with the above mentioned pathogenic *E. coli* control strains. Optimum PCR reactions for all primer/fluorigenic probes used were obtained at a MgCl$_2$ concentration of 5.2 mmol, 35 PCR cycles, an annealing temperature of 55° C. and an extension temperature of 65° C. Extension at 65° C. was found to yield higher RQ values, probably due to a lower rate of template/fluorogenic probe dissociation before degradation by Taq-polymerase.

The *E. coli* sltI gene was used as a target sequence for establishment of PCR and analysing different locations of probes relative to the PCR primers. Primers were designed to anneal in conserved regions of the sltI genes (see above). Two probes, sltI-N0 located 132 bp upstream of one primer and sltI-N1, placed at a 21 bp distance from the primer were compared. RQ values achieved with probe sltI-N1(RQ$_m$= 6.3800) were reproducably found higher than RQ values generated with probe sltI-N0 (RQ$_m$=0.9620) at equal template concentrations of the *E. coli* sltI control DNA. Generally, also probes specific for other target genes that were located close (4 to 20 bp) to one of the two PCR primers yielded consistently higher RQ values than probes that were placed at a greater distance from the primers.

The influence of DNA preparation on the performance of TAQMAN™-PCR was tested, since it has been reported that crude bacterial lysates can contain inhibiting factors that might interfere with PCR performance. Therefore, bacteria were collected after overnight growth on McConkey plates. DNA was prepared by boiling of bacteria inoculated in 0.9% NaCl solution or by isolation of genomic DNA with a commercial spin prep procedure (see the example, material and methods). The RQ values and sensititvity of TAQMAN™-PCR did not differ when the two preparation methods were compared. The RQ values obtained for PCR amplifications from DNA derived from 10$^5$ SltI or sltII containing EHEC prepared by boiling or by spin prep comparable.

The TAQMAN™-PCR method relies on the detection of free reporter dye (FAM) that is released from the probe after hydrolysis. Thus, probe concentration should also have an effect on the assay performance by affecting the fraction of the probe that is degraded during PCR cycling. Probe concentrations were titrated in the range of 100 pmol to 0.1 pmol and $\Delta$RQ values were determined. Optimal probe concentrations varied in between 10 pmol and 20 pmol depending on the target gene that was amplified.

For testing sensitivity of TAQMAN™-PCR, EHEC containing either sltI or sltII were diluted in a suspension containing *E. coli* strain ATCC11775 at 10$^7$ CfU at log step dilutions. PCR was performed under optimized conditions and results from ethidium-bromide stained agarose gels were compared to TaqMan™ results. Minimum detection limits of a sltI containing EHEC strain was 10$^3$ cfu within 10$^7$. For sltII the detection limit was found at 10$^{3.5}$ cfu in 10$^7$ enterobacteria. Both methods, detection of PCR products by agarose gel electrophoresis and measurement of fluorescence signals by the TaqMan method yielded comparable results, i.e. that at $\Delta$RQ values above $\Delta$RQ$_{threshold}$ PCR product bands were visible in agarose gelb whereas at $\Delta$RQ values around $\Delta$RQ threshold also in agarose gels PCR products were below the detection limit. After optimizing detection tests for all virulence factors/toxins, TAQMAN™-PCR was set up for routine testing of biological specimen for the presence of pathogenic *E. coli* bacteria. Results of TAQMAN™-PCR were compared to agarose gel electrophoresis.

The following example will illustrate the invention further. It is, however, not to be construed as limiting.

Example

1. Prevalence of Pathogenic *E. coli* in Stool Specimens from Children with Diarrhea was Tested Using the Method According to the Invention.

In order to verify TAQMAN™-PCR performance and to test for the occurence of pathogenic *E. coli* screening of 100 stool specimens from children of age 0 to 10 years with the clinical symptoms of diarrhea was undertaken. The materials and methods used in the test are described in more detail below under item 2.

Collection of specimen took place from June to October 1996. All samples in this study were derived from the area of Southern Bavaria. Stool specimen were plated on McConkey agar, incubated overnight and enterobacteria were collected. DNA was isolated and used as template in PCR reactions containing specific primers and fluorigenic probes for sltI, sltII, LT, ST, EAF-plasmid, eae-gene, inv-plasmid, and pCVD432. For verification of the integrity of DNA from individual preparations a control PCR reaction was set up, containing primers and an internal fluorigenic probe for amplification of the parC gene of *E. coli*. As a positive assay control, one PCR reaction was performed within each assay, where DNA from a positive control strain for the respective virulence factor/toxin was present. Applying this method reliable, specific and sensitive detection of all target genes could be achieved. Systematic analysis of 100 stool specimen derived from children suffering from diarrhea yielded 22 samples where one, two or three of the virulence factors/toxins of pathogenic *E. coli* could be detected. In detail, 2 patients harbored EHEC (one with hemorrhagic colitis and one developed HUS). 3 patients tested positive for ETEC, 16 for EPEC, 1 for EIEC, and 8 for EaggEC (see Table 4). The patient suffering from hemorrhagic colitis tested positive for sltI and eae, the patient developing HUS tested positive for sltI, sltII and eae. One patient simultaneously harbored ETEC (LT+,ST+), EPEC (eae+), and EaggEC (pCVD342+), one patient tested positive for EIEC (inv+) and EaggEC (pCVD342+), two stool specimen contained EPEC (eae+) and EaggEC (pCVD342).

Enterobacteria from the two patients with EHEC were hybridized with sltI and sltII gene probes for testing accuracy and specificity of TAQMAN™-PCR. In the case of patient one, where TAQMAN™-PCR was positive for sltI, only colonies hybridizing with sltI could be found. Colonies of patient two, where TAQMAN™-PCR was positive for sltI and sltII, hybridized with probes for sltI and sltII. Positive colonies were picked and biochemically typed as *E. coli*.

Antibiotic susceptibilty testing revealed that EHEC strains were sensitive to broad spectrum penicillins, cephalosporins and gyrase inhibitors.

2. Materials and Methods a) Bacterial strains, media, culture and DNA preparation: A number of EHEC, ETEC, EPEC, EIEC, and EaggEC *E. coli* strains were used as controls for accurate PCR amplification and were kindly provided by H. Karch, Würzburg, Germany and H. Beutin, Berlin, Germany (see Table 1) As a strain not harboring these virulence genes *E. coli* ATCC 11775 was used. For TaqMan™-PCR optimization, positive control strains were grown on McConkey agar (Becton Dickinson, Germany) at 37° C. After overnight culture, bacteria were collected and resuspended in 0.9% NaCl solution. Turbidity was adjusted to McFarland 0.5. DNA was either prepared by boiling (950° C, 10 min) or isolated using QiaAmp tissue kit spin prep columns (Qiagen, Germany). 10 µl of DNA suspension was used for PCR. Detection of pathogenic *E. coli* strains from stool specimen of humans or cows was performed after spreading an appropriate amount of stool on McConkey plates. After overnight culture all bacterial colonies from the surface of the McConkey plates were collected and processed as detailed above.

b) PCR-cyling: PCR recations were set up in 70 µl final volume in thin-walled 0.2 ml "optical PCR-tubes" (Perkin Elmer, Germany). The reaction mix contained: 10 µl of bacterial lysate, 5.25 µl 25 mmol $MgCl_2$, 7 µl 10×PCR buffer, 40 pmol primers, 20 pmol specific fluorogenic probe, 150 µM of each dATP, dTTP, dGTP, dCTP (Perkin Elmer), 1 U AmpliTaq-Polymerase (Perkin Elmer). A Perkin Elmer model 9600 thermal cycler was used for PCR cycling. Initial denaturation of bacterial DNA was performed by heating for 5 min to 94° C. All cycles included a denaturation step for 15 sec at 94° C., annealing for 1 min 30 sec at 55° C., and extension for 1 min 30 sec at 65° C. 35 cycles were performed.

c) Post-PCR processing: After completion of cycling, the fluorescence intensities of the reporter dye, FAM, and the quencher dye, TAMRA, were determined using a Perkin Elmer LS50B luminiscence spectrophotometer equipped with a plate reader and modified for fluorescence measurements of PCR reactions in optical tubes. ΔRQ values were calculated as described in (74). A $ARQ_{threshold}$ value was calculated on the basis of a 99% confidence interval above the mean of the triplicate no template controls ($\Delta RQ_{threshold}$ = 6,95×$std_{mean\ of\ no\ template\ controls}$). PCR reactions were scored positive if $\Delta RQ_{sample} > \Delta RQ_{threshold}$ was given. For verification of the sensitivity of TaqMan™-measurements, PCR products were subjected to agarose gel electrophoresis. 15 µl of sample were loaded with 2 µl sample buffer. PCR products were separated in 2% agarose gels containing ethidium bromide at 100V for 35 min. DNA was visualized under UV light and a digital image file was obtained using the Eagle EyeII System (Stratagene).

d) Verification of PCR amplificates: PCR products obtained from templates of respective positive control strains were directly subcloned into the TA cloning vector (Invitrogen, Germany) for verification of specificity of PCR amplification. After transfection ($CaCl_2$-method) of DH5α bacteria with the ligation products, plasmid containing bacteria were selected on ampicillin (Sigma, Germany) containing LB plates. Plasmid DNA was purified with Qiagen DNA purification columns (Quiagen, Germany). Inserts were PCR-cycle sequenced employing dideoxy-nucleotides conjugated to 4 dyes (DNA Dye terminator cycle sequencing kit, Perkin Elmer, Germany). Sequences were obtained with an Applied Biosystems model 373A (Applied Biosystems, Germany). Insert sequences were aligned to published sequences as referenced in Table 1 using the McDNAsis programme (Appligene, Great Britain). Sequence comparisons verified that the PCR products were identical to the respective virulence factors or toxins.

e) Sensitivity of TAQMAN™ technique: For determination of the sensitivity of the TAQMAN™ method, serial log-step dilutions of positive control strains were performed in a solution containing $10^7$ cfu of *E. coli* reference strain ATCC 11775 DNA was either prepared by the boiling method (see above) or purified using spin prep columns designed for isolation of genomic bacterial DNA (Qiagen, Germany). Purification was according to the protocol of the manufacturer. The detection limit for sltI containing strains was determined with $10^3$ cfu among $10^7$ *E. coli* and for sltII containing strains as $10^{3.5}$ among $10^7$.

f) Colony hybridisation and isolation of EHEC bacteria: EHEC bacterial strains and stool samples from patients testing positive in sltI or sltII TAQMAN™-PCR were subjected to colony hybridisation. Briefly, bacteria were plated on-McConkey agar plates such that single colonies could be seen. Bacteria were blotted on nylon membranes (Genescreen Plus, NEN, Germany), cracked (1% SDS), denatured (0.5M NaOH, 1.5M NaCl), neutralized (1M TRIS, 1.5M NaCl), and washed (20×SSC). Membranes were baked at 80° C. for 2 hours. DNA probes specific for sal or sltII were labelled with fluorescein (Gene-Images random prime labelling module, Amersham, Germany).

Afterwards, filters were hybridized with labelled probes. Hybridization was verified by non-radioactive detection system employing anti-FITC peroxidase mAb and ECL detection module (Gene Images CDP-Star detection module, Amersham, Germany). Bacterial colonies hybridizing with the probe and non-hybridizing colonies were picked, verified by TAQMAN™-PCR and tested for antibiotic susceptibility. Antibiotic susceptibility testing. EHEC and non-EHEC *E. coli* were picked from McConkey plates after testing for sltI or sltII or both toxin genes in colony hybridazation and MIC testing was performed according to NCCLS guidelines for enterobacteria.

TABLE 1

*E. coli* strains - virulence factors/toxins

| Group | Strain number | Serotype | Virulence factor/toxin |
|---|---|---|---|
| EHEC | 1193/89 | O157:H- | sltI, ene |
|  | 3574/92 | O157:H7 | sltII, ene |
|  | A9167C | O157:H7 | sltI, sltIIc, ene |
|  | 5769/87 | O157:H7 | sltI, sltII, eae |
|  | 427/89 | O157:H- | sltI, sltIIc, ene |
|  | 1249/87 | O157:H7 | sltII, sltIIc, ene |
| ETEC | 147/1 | O128:H- | ST |
|  | 164/82 | O148:H28 | LT |
| EPEC | 111/87 | O111 | EAF, ene |
|  | 12810 | O114:H2 | EAF, eae |
| EIEC | 76-5 | O143 | inv-plasmid |
|  | 12860 | O124 | inv-plasmid |
| EaggEC |  |  | pCVD432 plasmid |
| control | ATCC 11775 |  | — |

TABLE 2

Primers for detection of pathogenic *E. coli*. W is A/T, R is A/G, D is A/G/T, Y is C/T and K is G/T.

| Group | Virulence factor/toxin | Primer | Sequence (5' → 3') | location of primer | Size of PCR product | Genbank Ref. | Ref. |
|---|---|---|---|---|---|---|---|
| ETEC | LT | LT-1 | gcg tta cta tcc tct cta tgt g (SEQ ID NO: 1) | 874–895 | 339 | S60731 | (84) |
|  |  | LT-2 | agt ttt cca tac tga ttg ccg c (SEQ ID NO: 2) | 1213–1192 |  |  |  |
|  | ST | ST-1 | tcc ctc agg atg cta aac cag (SEQ ID NO: 3) | 100–120 | 260 | M34916 | (36) |
|  |  | ST-2a | tcg att tat tca aca aag caa c (SEQ ID NO: 4) | 360–339 |  |  |  |
| EaggEC | pCVD432 plasmid | EA-1 | ctg gcg aaa gac tgt atc att g (SEQ ID NO: 7) | 66–87 | 629 | X81423 | (40, 50) |
|  |  | EA-2 | taa tgt ata gaa atc cgc tgt t (SEQ ID NO: 8) | 695–674 |  |  |  |
| EIEC | inv-plasmid | EI-1 | ttt ctg gat ggt atg gtg agg (SEQ ID NO: 9) | 17786–17806 | 303 | D50601 emb | (38, 48) |
|  |  | EI-2 | ctt gaa cat aag gaa ata aac (SEQ ID NO: 10) | 18089–18069 |  |  |  |
| EPEC | EAF plasmid | EP-1 | cag ggt aaa aga aag atg ata ag (SEQ ID NO: 11) | 546–568 | 398 | X76137 | (37, 85) |
|  |  | EP-2 | aat atg ggg acc atg tat tat c (SEQ ID NO: 12) | 944–923 |  |  |  |
|  | eae | EPeh-1 | ccc gga ccc ggc aca agc ata ag (SEQ ID NO: 13) | 91–113 | 872 | Z11541 | (86) |
|  |  | EPeh-2 | agt ctc gcc agt att cgc cac c (SEQ ID NO: 14) | 963–942 |  |  |  |
| EHEC | sltI | sltI-1 | atg aaa aaa aca tta tta ata gc (SEQ ID NO: 15) | 1113–1135 | 287 | Z36899 | (77, 78) |
|  |  | sltI-2 | tca cyg agc tat tct gag tca acg (SEQ ID NO: 16) | 1400–1376 |  |  |  |
|  | sltII | sltII-1 | atg aag aag atr wtt rtd gcr gyt tta tty g (SEQ ID NO: 17) | 1148–1178 | 265 | L11079 | (79–83) |
|  |  | sltII-2 | tca gtc atw att aaa ctk cac yts rgc aaa kcc (SEQ ID NO: 18) | 1413–1385 |  |  |  |
| control | parC | par-1 | aac ctg ttc agc gcc gca ttg (SEQ ID NO: 28) | 141–161 | 260 | M58408 | (87) |
|  |  | par-2 | aca acc ggg att ccg tgt aac (SEQ ID NO: 29) | 401–381 |  |  |  |

TABLE 3

TaqMan ™-probes used for detection of pathogenic E. coli

| Group | virulence factor/ toxin | Probe for Taqman ™ (FAM-5' → 3'-TAMRA) | bp | Gen-bank Ref. | Ref. |
|---|---|---|---|---|---|
| ETEC | LT | agc tcc cca gtc tat tac aga act atg (SEQ ID NO:19) | 903–929 | S60731 | (84) |
|  | ST | aca tac gtt aca gac ata atc aga atc ag (SEQ ID NO:20) | 334–306 | M34916 | (36) |
| EaggEC | pCVD432 plasmid | ctc ttt taa ctt atg ata tgt aat gtc tgg (SEQ ID NO:22) | 668–639 | X81423 | (40, 50) |
| EIEC | inv - plasmid | caa aaa cag aag aac cta tgt cta cct (SEQ ID NO:23) | 18063–18037 | D50601 emb | (38, 48) |
| EPEC | EAF - plasmid | ctt gga gtg atc gaa cgg gat cca aat (SEQ ID NO:24) | 575–601 | X76137 | (37, 85) |
|  | eae | taa acg ggt att atc acc aga aaa atc c (SEQ ID NO:25) | 935–908 | Z11541 | (86) |
| EHEC | sltI | tcg ctg aat ccc cct cca tta tga cag gca (SEQ ID NO:26) | 1367–1338 | Z36899 | (77, 78) |
|  | sltII | cag gta ctg gat ttg att gtg aca gtc att (SEQ ID NO:27) | 1371–1342 | L11079 | (79–83) |
| control | parC | atg tct gaa ctg ggc ctg aat gcc agc (SEQ ID NO:30) | 169–199 | M58408 | (87) |

TABLE 4

Frequency of pathogenic E. coli in stool samples of children with diarrhea (n = 100)

| Group | virulence factor/ toxin | TaqMan: number of positive isolates | Agar gel electrophores is: number of positive isolates | pathogenic group |
|---|---|---|---|---|
| ETEC | LT | 2 | 2 | 5 |
|  | ST | 3 | 3 |  |
| EaggEC | 60 kb plasmid | 8 | 8 | 8 |
| EIEC | inv plasmid | 1 | 1 | 1 |
| EPEC | EAF plasmid | 1 | 1 | 16 |
|  | eae | 15 | 15 |  |
| EHEC | sltI | 2 | 2 | 2 |
|  | sltII | 1 | 1 |  |
| control | parC | 100 | 100 |  |

References:

1. Centers for Disease Control.1982. Isolation of *E. coli* O157:H7 from sporadic cases of hemorrhagic colitis—United States. *MMWR. Morb. Mortal. Wkly. Rep.* 31:580, 585.
2. Karmali, M. A., M. Petric, C. Lim, P. C. Fleming, and B. T. Steele. 1983. *Escherichia coli* cytotoxin, haemolytic-uraemic syndrome, and haemorrhagic colitis [letter]. *Lancet* 2:1299.
3. Karmali, M. A., M. Petric, C. Lim, and P. C. Fleming. 1985. The association between idiopatic hemolitic uremic syndrom and infection by verotoxin-producing *Escherichia coli*. *J. Infect. Dis.* 151:775.
4. Riley, L. W., R. S. Remis, S. D. Helgerson, H. B. McGee, J. G. Wells, B. R. Davis, R. J. Hebert, E. S. Olcott, L. M. Johnson, N. T. Hargrett, P. A. Blake, and M. L. Cohen. 1983. Hemorrhagic colitis associated with a rare *Escherichia coli* serotype. *N. Engl. J. Med.* 308:681.
5. Pai, C. H., R. Gordon, H. V. Sims, and L. E. Bryan. 1984. Sporadic cases of hemorrhagic colitis associated with *Escherichia coli* O157:H7. Clinical, epidemiologic, and bacteriologic features. *Ann. Intern. Med.* 101:738.
6. Borczyk, A. A., M. A. Karmali, H. Lior, and L. M. Duncan. 1987. Bovine reservoir for verotoxin-producing *Escherichia coli* O157: H7 [letter]. *Lancet* 1:98.
7. Blanco, J. E., M. Blanco, and J. Blanco. 1995. [Enterotoxigenic, verotoxigenic, and necrotoxigenic *Escherichia coli* in food and clinical samples. Role of animals as reservoirs of strains pathogenic for humans]. *Microbiologia*. 11:97.
8. Ostroff, S. M., P. M. Griffin, R. V. Tauxe, L. D. Shipman, K. D. Greene, J. G. Wells, J. H. Lewis, P. A. Blake, and J. M. Kobayashi. 1990. A statewide outbreak of *Escherichia coli* O157:H7 infections in Washington State. *Am. J. Epidemiol.* 132:239.
9. Centers for Disease Control. 1993. Update: multistate outbreak of *Escherichia coli* O157:H7 infections from hamburgers-western United States, 1992–1993. *MMWR* 42:258.
10. Nathan, R. 1996. Japans *E. coli* outbreak elicits fear, anger. *Nature Medicine* 2:956.
11. Griffin, P. M., S. M. Ostroff, R. V. Tauxe, K. D. Greene, J. G. Wells, J. H. Lewis, and P. A. Blake. 1988. Illnesses associated with *Escherichia coli* O157:H7 infections. A broad clinical spectrum. *Ann. Intern. Med.* 109:705.
12. Karmali, M. A. 1989. Infection by verocytotoxin-producing *Escherichia coli*. *Clin. Microbiol. Rev.* 2:15.
13. Kovacs, M. J., J. Roddy, S. Gregoire, W. Cameron, L. Eidus, and J. Drouin. 1990. Thrombotic thrombocytopenic purpura following hemorrhagic colitis due to *Escherichia coli* O157:H7. *Am. J. Med.* 88:177.
14. O'Brien, A. D. and R. K. Holmes. 1987. Shiga and Shiga-like toxins. *Microbiol. Rev.* 51:206.
15. Karch, H. and J. Bockemühl. 1989. [Infections by enterohemorrhagic *Escherichia coli* (EHEC): a clinical and microbiologic problem and a challenge for the public health service]. *Immun. Infekt.* 17:206.
16. Siegler, R. L. 1995. The hemolytic uremic syndrome. *Pediatr. Clin. North Am.* 42:1505.
17. Rowe, P. C., W. Walop, H. Lior, and A. M. Mackenzie. 1991. Haemolytic anaemia after childhood *Escherichia coli* O 157 .H7 infection: are females at increased risk? *Epidemiol. Infect.* 106:523.
18. 1996. Häufung von EHEC-Erkrankungen in Bayern. Münclner Ärztliche Anzeigen 23:14.

19. Doyle, M. P. 1991. *Escherichia coli* O157:H7 and its significance in foods. *Int. J. Food Microbiol.* 12:289.
20. Belongia, E. A., K. L. MacDonald, G. L. Parham, K. E. White, J. A. Korlath, M. N. Lobato, S. M. Strand, K. A. Casale, and M. T. Osterholm. 1991. An outbreak of *Escherichia coli* O157:H7 colitis associated with consumption of precooked meat patties. *J. Infect. Dis.* 164:338.
21. O'Brien, A. D., A. R. Melton, C. K. Schmitt, M. L. McKee, M. L. Batts, and D. E. Griffin. 1993. Profile of *Escherichia coli* O157:H7 pathogen responsible for hamburger-borne outbreak of hemorrhagic colitis and hemolytic uremic syndrome in Washington. *J. Clin. Microbiol.* 31:2799.
22. Beutin, L., D. Geier, H. Steinruck, S. Zimmermann, and F. Scheutz. 1993. Prevalence and some properties of verotoxin (Shiga-like toxin)-producing Escherichia coli in seven different species of healthy domestic animals. *J. Clin. Microbiol.* 31:2483.
23. Martin, M. L., L. D. Shipman, J. G. Wells, M. E. Potter, K. Hedberg, I. K. Wachsmuth, R. V. Tauxe, J. P. Davis, J. Arnoldi, and J. Tilleli. 1986. Isolation of *Escherichia coli* O157:H7 from dairy cattle associated with two cases of haemolytic uraemic syndrome [letter]. Lancet 2:1043.
24. Besser, R. E., S. M. Lett, J. T. Weber, M. P. Doyle, T. J. Barrett, J. G. Wells, and P. M. Griffin. 1993. An outbreak of diarrhea and hemolytic uremic syndrome from *Escherichia coli* O157:H7 in fresh-pressed apple cider [see comments]. *JAMA* 269:2217.
25. Read, S. C., C. L. Gyles, R. C. Clarke, H. Lior, and S. McEwen. 1990. Prevalence of verocytotoxigenic *Escherichia coli* in ground beef, pork, and chicken in southwestern Ontario. *Epidenziol. Infect.* 105:11.
26. Gannon, V. P., R. K. King, J. Y. Kim, and E. J. Thomas. 1992. Rapid and sensitive method for detection of Shiga-like toxin-producing *Escherichia coli* in ground beef using the polymerase chain reaction. *Appl. Environ. Microbiol.* 58:3809.
27. Bopp, C. A., K. D. Greene, F. P. Downes, E. G. Sowers, J. G. Wells, and I. K. Wachsmuth. 1987. Unusual verotoxin-producing *Escherichia coli* associated with hemorrhagic colitis. J. Clin. Microbiol. 25:1486.
28. Farmer, J. J. and B. R. Davis. 1985. H7 antiserum-sorbitol fermentation medium: a single tube screening medium for detecting *Escherichia coli* O157:H7 associated with hemorrhagic colitis. *J. Clin. Microbiol.* 22:620.
29. Scotland, S. M., B. Rowe, H. R. Smith, G. A. Willshaw, and R. J. Gross. 1988. Vero cytotoxin-producing strains of *Escherichia coli* from children with haemolytic uraemic syndrome and their detection by specific DNA probes. *J. Med. Microbiol.* 25:237.
30. Scotland, S. M., G. A. Willshaw, H. R. Smith, B. Said, N. Stokes, and B. Rowe. 1993. Virulence properties of *Escherichia coli* strains belonging to serogroups O26, O55, O111 and O128 isolated in the United Kingdom in 1991 from patients with diarrhoea. Epidemiol. Infect 111:429.
31. Russmann, H., E. Kothe, H. Schmidt, S. Franke, D. Harmsen, A. Caprioli, and H. Karch. 1995. Genotyping of Shiga-like toxin genes in non-O157 *Escherichia coli* strains associated with haemolytic uraemic syndrome. *J. Med. Microbiol.* 42:404.
32. Koneman, E. W., S. D. Allen, W. M. Janda, P. C. Schreckenberger, and C. W. j. Washington. 1992. The Enterobacteriaceae. In Diagnostic Microbiology. J.B. Lippincott Company, Philadelphia. 132–133.
33. Edelman, R. and N. F. Pierce. 1984. From the National Institute of Allergy and Infectious Diseases. Summary of the 19th United States-Japan Joint Cholera Conference. *J. Infect. Dis.* 149:1014.
34. Hart, C. A., R. M. Batt, and J. R. Saunders. 1993. Diarrhoea caused by *Escherichia coli. Ann. Trop. Paediatr.* 13:121.
35. Chapman, P. A. and C. M. Daly. 1993. Evaluation of non-radioactive trivalent DNA probe (LT, ST1a, ST1b) for detecting enterotoxigenic *Escherichia coli. J. Clin. Pathol.* 46:309.
36. Moseley, S. L., J. W. Hardy, M. I. Hug, P. Echeverria, and S. Falkow. 1983. Isolation and nucleotide sequence determination of a gene encoding a heat-stable enterotoxin of *Escherichia coli. Infect. Immun.* 39:1167.
37. Jerse, A. E., J. Yu, B. D. Tall, and J. B. Kaper. 1990. A genetic locus of enteropathogenic *Escherichia coli* necessary for the production of attaching and effacing lesions on tissue culture cells. *Proc. Natl. Acad. Sci. U.S.A.* 87:7839.
38. Taylor, D. N., P. Echeverria, 0. Sethabutr, C. Pitarangsi, U. Leksomboon, N. R. Blacklow, B. Rowe, R. Gross, and J. Cross. 1988. Clinical and microbiologic features of Shigella and enteroinvasive *Escherichia coli* infections detected by DNA hybridization. *J. Clin. Microbiol.* 26:1362.
39. Prats, G. and T. Llovet. 1995. [Enteroinvasive *Escherichia coli*. Pathogenesis and epidemiology]. *Microbiologia.* 11:91.
40. Nataro, J. P., Y. Deng, D. R. Maneval, A. L. German, W. C. Martin, and M. M. Levine. 1992. Aggregative adherence fimbriae I of enteroaggregative *Escherichia coli* mediate adherence to HEp-2 cells and hemagglutination of human erythrocytes. *Infect. Immun.* 60:2297.
41. Cohen, M. B., J. A. Hawkins, L. S. Weckbach, J. L. Staneck, M. M. Levine, and J. E. Heck. 1993. Colonization by enteroaggregative *Escherichia coli* in travelers with and without diarrhea. *J. Clint. Microbiol.* 31:351.
42. Chang, P. P., J. Moss, E. M. Twiddy, and R. K. Holmes. 1987. Type II heat-labile enterotoxin of *Escherichia coli* activates adenylate cyclase in human fibroblasts by ADP ribosylation. *Infect. Immun.* 55:1854.
43. Pickett, C. L., D. L. Weinstein, and R. K. Holmes. 1987. Genetics of type IIa heat-labile enterotoxin of *Escherichia coli*: operon fusions, nucleotide sequence, and hybridization studies. *J. Bacteriol.* 169:5180.
44. Giron, J. A., M. S. Donnenberg, W. C. Martin, K. G. Jarvis, and J. B. Kaper. 1993. Distribution of the bundle-forming pilus structural gene (bfpA) among enteropathogenic *Escherichia coli. J. Infect. Dis.* 168:1037.
45. Karch, H., J. Heesemann, R. Laufs, A. D. O'Brien, C. O. Tacket, and M. M. Levine. 1987. A plasmid of enterohemorrhagic *Escherichia coli* O157:H7 is required for expression of a new fimbrial antigen and for adhesion to epithelial cells. *Infect. Immun.* 55:455.
46. Nataro, J. P., M. M. Baldini, and J. B. Kaper. 1985. Detection of an Adherence Factor of Enteropathogenic *Eschierichia coli* with a DNA probe. *J. Infect. Dis.* 152:560.
47. Watanabe, H., E. Arakawa, K. Ito, J. Kato, and A. Nakamura. 1990. Genetic analysis of an invasion region by use of a Tn3-lac transposon and identification of a second positive regulator gene, invE, for cell invasion of *Shigella sonnei:* significant homology of invE with ParB of plasmid P1. *J. Bacteriol.* 172:619.
48. Sasakawa, C., K. Komatsu, T. Tobe, T. Suzuki, and M. Yoshikawa. 1993. Eight genes in region 5 that form an operon are essential for invasion of epithelial cells by *Shigella flexneri* 2a. *J. Bacteriol.* 175:2334.

49. Echeverria, P., O. Serichantalerg, S. Changchawalit, B. Baudry, M. M. Levine, F. Orskov, and I. Orskov. 1992. Tissue culture-adherent *Escherichia coli* in infantile diarrhea. *J. Infect. Dis.* 165:141.
50. Schmidt, H., C. Knop, S. Franke, S. Aleksic, J. Heesemann, and H. Karch. 1995. Development of PCR for screening of enteroaggregative*Escherichia coli*. *J. Clin. Microbiol.* 33:701.
51. Faruque, S. M., K. Haider, M. M. Rahman, A. R. Abdul Alim, A. H. Baqui, Q. S. Ahmad, K. M. Hossain, and M. J. Albert. 1992. Evaluation of a DNA probe to identify enteroaggregative *Escherichia coli* from children with diarrhoea in Bangladesh. *J. Diarrhoeal. Dis. Res.* 10:31.
52. Yamamoto, T., P. Echeverria, and T. Yokota. 1992. Drug resistance and adherence to human intestines of enteroaggregative *Escherichia coli*. *J. Infect. Dis.* 165:744.
53. Savarino, S. J., A. Fasano, J. Watson, B. M. Martin, M. M. Levine, S. Guandalini, and P. Guerry. 1993. Enteroaggregative *Escherichia coli* heat-stable enterotoxin 1. represents another subfamily of *E. coli* heat-stable toxin. *Proc. Natl. Acad. Sci. U.S.A.* 90:3093.
54. Bennett, A. R., S. MacPhee, and R. P. Betts. 1995. Evaluation of methods for the isolation and detection of *Escherichia coli* O157 in minced beef. *Lett. Appl. Microbiol.* 20:375.
55. March, S. B. and S. Ratnam. 1986. Sorbitol-MacConkey medium for detection of *Escherichia coli* O157: H7 associated with hemorrhagic colitis. *J. Clin. Microbiol.* 23:869.
56. Kleanthous, H., N. K. Fry, H. R. Smith, R. J. Gross, and B. Rowe. 1988. The use of sorbitol-MacConkey agar in conjunction with a specific antiserum for the detection of Vero cytotoxin-producing strains of *Escherichia coli* O157. Epidemiol. Infect. 101:327.
57. March, S. B. and S. Ratnam. 1989. Latex agglutination test for detection of *Escherichia coli* serotype O157. *J. Clin. Microbiol.* 27:1675.
58. Beutin, L., S. Aleksic, S. Zimmermann, and K. Gleier. 1994. Virulence factors and phenotypical traits of verotoxigenic strains of *Escherichia coli* isolated from human patients in Germany. *Med. Microbiol. Immunol. Berl.* 183:13.
59. Stroeher, U. H., L. Bode, L. Beutin, and P. A. Manning. 1993. Characterization and sequence of a 33-kDa enterohemolysin (Ehly 1)-associated protein in *Escherichia coli*. Gene 132:89.
60. Johnson, R. P., R. J. Durham, S. T. Johnson, L. A. MacDonald, S. R. Jeffrey, and B. T. Butman. 1995. Detection of *Escherichia coli* O157:H7 in meat by an enzyme-linked immunosorbent assay, EHEC-Tek. *Appl. Environ. Microbiol.* 61:386.
61. Padhye, N. V. and M. P. Doyle. 1991. Rapid procedure for detecting enterohemorrhagic *Escherichia coli* O157:H7 in food. *Appl. Environ. Microbiol.* 57:2693.
62. Clark, C. G., S. Johnson, and R. P. Johnson. 1995. Further characterisation of a monoclonal antibody reactive with *Escherichia coli* O157:H7. *J. Med. Microbiol.* 43:262.
63. Karmali, M. A., M. Petric, M. Winkler, M. Bielaszewska, J. Brunton, N. van de Kar, T. Morooka, G. B. Nair, S. E. Richardson, and G. S. Arbus. 1994. Enzyme-linked immunosorbent assay for detection of immunoglobulin G antibodies to *Escherichia coli* Vero cytotoxin 1. *J. Clin. Microbiol.* 32:1457.
64. Gunzer, F., H. Bohm, H. Russmann, M. Bitzan, S. Aleksic, and H. Karch. 1992. Molecular detection of sorbitol-fermenting *Escherichia coli* O157 in patients with hemolytic-uremic syndrome. *J. Clin. Microbiol.* 30:1807.
65. Bockemuhl, J., S. Aleksic, and H. Karch. 1992. Serological and biochemical properties of Shiga-like toxin (verocytotoxin)-producing strains of *Escherichia coli*, other than O-group 157, from patients in Germany. *Int. J. Med. Microbiol. Virol. Parasitol. Infect. Dis.* 276:189.
66. Smith, H. R., S. M. Scotland, G. A. Willshaw, C. Wray, I. M. McLaren, T. Cheasty, and B. Rowe. 1988. Vero cytotoxin production and presence of VT genes in *Escherichia coli* strains of animal origin. *J. Gen. Microbiol.* 134:829.
67. Karch, H. and T. Meyer. 1989. Evaluation of oligonucleotide probes for identification of shiga-like-toxin-producing *Escherichia coli*. *J. Clin. Microbiol.* 27:1180.
68. Jackson, M. P. 1991. Detection of Shiga Toxin-Producing Shighella dysenteriae Type 1 and *Escherichia Coli* by Using Polymerase Chain Reaction with Incorporation of Digixigenin-11-dUTP. *J. Clin. Microbiol.* 29:1910.
69. Johnson, W. M., D. R. Pollard, H. Lior, S. D. Tyler, and K. R. Rozee. 1990. Differentiation of genes coding for *Escherichia coli* verotoxin 2 and the verotoxin associated with porcine edema disease (VTe) by the polymerase chain reaction. *J. Clin. Microbiol.* 28:2351.
70. Johnson, W. M., S. D. Tyler, G. Wang, and H. Lior. 1991. Amplification by the polymerase chain reaction of a specific target sequence in the gene coding for *Escherichia coli* verotoxin (VTe variant). *FEMS Microbiol. Lett.* 68:227.
71. Karch, H. and T. Meyer. 1989. Single primer pair for amplifying segments of distinct shiga-like-toxin genes by polymerase chain reaction. *J. Clin. Microbiol.* 27:2751.
72. Pollard, D. and W. M. Johnson. 1990. Rapid and Specific Detection of Verotoxin Genes in *Escherichia Coli* by the Polimerase Chain Reaction. *J. Clin. Microbiol.* 28:540.
73. Holland, P. M., R. D. Abramson, R. Watson, and D. H. Gelfand. 1991. Detection of specific polymerase chain reaction product by utilizing the 5'-3' exonuclease activity of Thermus aquaticus DNA polymerase. *Proc. Natl. Acad. Sci. U.S.A.* 88:7276.
74. Bassler, H. A., S. J. Flood, K. J. Livak, J. Marmaro, R. Knorr, and C. A. Batt. 1995. Use of a fluorogenic probe in a PCR-based assay for the detection of Listeria monocytogenes. *Appl. Environ. Microbiol.* 61:3724.
75. Livak, K. J., S. J. Flood, J. Marmaro, W. Giusti, and K. Deetz. 1995. Oligonucleotides with fluorescent dyes at opposite ends provide a quenched probe system useful for detecting PCR product and nucleic acid hybridization. *PCR. Methods Appl.* 4:357.
76. Förster, V. 1948. Zwischenmolekulare Energiewanderung und Fluoreszenz. *Annals of Physics (Leipzig)* 2:55.
77. Paton, A. W., J. C. Paton, P. N. Goldwater, and P. A. Manning. 1993. Direct detection of *Escherichia coli* Shiga-like toxin genes in primary fecal cultures by polymerase chain reaction. *J. Clin. Microbiol.* 31:3063.
78. Paton, A. W., J. C. Paton, P. N. Goldwater, M. W. Heuzenroeder, and P. A. Manning. 1993. Sequence of a variant Shiga-like toxin type-I operon of *Escherichia coli* O111:H-. Gene 129:87.
79. Paton, A. W., J. C. Paton, and P. A. Manning. 1993. Polymerase chain reaction amplification, cloning and sequencing of variant *Escherichia coli* Shiga-like toxin type II operons. *Microb. Pathog.* 15:77.
80. Gyles, C. L., S. A. De Grandis, C. MacKenzie, and J. L. Brunton. 1988. Cloning and nucleotide sequence analysis of the genes determining verocytotoxin production in a porcine edema disease isolate of *Escherichia coli*. *Microb. Pathog.* 5:419.

81. Gannon, V. P., C. Teerling, S. A. Masri, and C. L. Gyles. 1990. Molecular cloning and nucleotide sequence of another variant of the *Escherichia coli* Shiga-like toxin II family. *J. Gen. Microbiol.* 136:1125.
82. Schmitt, C. K., M. L. McKee, and A. D. O'Brien. 1991. Two copies of Shiga-like toxin II-related genes common in enterohemorrhagic *Escherichia coli* strains are responsible for the antigenic heterogeneity of the O157:H-strain E32511. *Infect. Immun.* 59:1065.
83. Schmidt, H., M. Montag, J. Bockemuhl, J. Heesemann, and H. Karch. 1993. Shiga-like toxin II-related cytotoxins in *Citrobacter freundii* strains from humans and beef samples. *Infect. Immun.* 61:534.
84. Inoue, T., T. Tsuji, M. Koto, S. Imamura, and A. Miyama. 1993. Amino acid sequence of heat-labile enterotoxin from chicken enterotoxigenic *Escherichia coli* is identical to that of human strain H 10407. *FEMS Microbiol. Lett.* 108:157.
85. Franke, J., H. Schmidt, and H. Karch. 1994. Nucleotide Sequence Analysis of Enteropathogenic *Escherichia coli* (EPEC) Adherence Factor Probe and Development of PCR for Rapid Detection of EPEC Harboring Virulence Plasmids. *J. Clin. Microbiol.* 32:2460.
86. Yu, J. and J. B. Kaper. 1992. Cloning and characterization of the eae gene of enterohaemorrhagic *Escherichia coli* O157:H7. *Mol. Microbiol.* 6:411.
87. Kato, J., Y. Nishimura, R. Imamura, H. Niki, S. Hiraga, and H. Suzuki. 1990. New topoisomerase essential for chromosome segregation in *E. coli* [published erratum appears in Cell 1991 Jun. 28;65(7):1289]. *Cell* 63:393.
88. Zhao, S., S. E. Mitchell, J. Meng, M. P. Doyle, and S. Kresovich. 1995. Cloning and nucleotide sequence of a gene upstream of the eaeA gene of enterohemorrhagic *Escherichia coli* O157:H7. *FEMS Microbiol. Lett.* 133:35.
89. Paton, A. W. and J. C. Paton. 1996. *Enterobacter cloacae* producing a shiga-like toxin II-related cytotoxinn associated with a case of hemolytic-uremic syndrome. *J. Clin. Microbiol.* 34:463.
90. Witham, P. K., K. J. Livak, C. A. Batt, and C. T. Yamashiro. 1996. A PCR-based assay for detection of *Escherichia coli* shiga-like toxin genes in ground beef. *Appl. Environ. Microbiol* 62:1347.
91. Karch, H., C. Janetzki-Mittmann, S. Aleksic, and M. Datz. 1996. Isolation of Enterohemorrhagic *Escherichia coli* O157 strains from patients with hemolytic-uremic symdrome by using immunomagnetic separation, DNA-based methods, and direct culture. *J. Clin. Microbiol.* 34:516.
92. Huppertz, H. I., D. Busch, H. Schmidt, S. Aleksic, and H. Karch. 1996. Diarrhea in young children associated with *Escherichia coli* non-O157 organisms that produce shiga-like toxin. *J. Pediatrics* 128:341.

---

What is claimed is:

1. A method for detection and differentiation of pathogenic enterobacteria in a sample, said method comprising:
  isolating nucleic acid from said sample;
  adding a set of oligonucleotide primer pairs to said nucleic acid sample wherein said set of oligonucleotide primers comprises at least five oligonucleotide primer pairs wherein, wherein each primer pair specifically amplifies a DNA sequence of a virulence factor/toxin gene characteristic for one each of the subgroups of the pathogenic E. coli strains, said subgroups comprising enterotoxigenic, enteroaggregative, enteroinvasive, enteropathogenic and enterohemorrhagic E. coli strains and wherein for amplification of each subgroup at least one oligonucleotide primer pair is included in said set of oligonucleotide primer pairs, and wherein the set comprises a primer pair that hybridizes to an inv-plasmid of enteroinvasive E. coli and wherein said primer pair is El-1: 5"TTT CTG GAT GGT ATG GTG AGG 3' (SEQ ID NO: 9) and E1-2: 5'CTT GAA CAT AAG GAA ATA AAC 3' (SEQ ID NO: 10) which specifically amplifies a DNA sequence of an inv plasmid characteristic for enteroinvasive E. coli; and
  subjecting said nucleic acid and said set of primer pairs to an amplification process; and
  detecting the presence of at least one amplified product, wherein the presence of at least one amplified product indicates the presence of at least one pathogenic enterobactcria strain in said sample.

2. The method according to claim 1, wherein the set of oligonucleotide primer pairs comprises primer pairs selected from the group consisting of:
  at least one primer pair that hybridizes to a gene encoding heat labile toxin or a gene encoding heat stabile toxin for amplification of a DNA sequence characteristic for enterotoxigenic E. coli;
  at least one primer pair that hybridizes to a gene encoding heat stabile toxin or to a pCDVD432 plasmid for amplification of a DNA sequence characteristic for enteroaggregative E. coli;
  at least one primer pair that hybridizes to a EAF plasmid, or an eae gene for amplification of a DNA sequence characteristic for enteropathogenic E. coli; and
  at least one primer pair that hybridizes to genes encoding shiga-like toxin sltI or sltII for amplification of a DNA sequence characteristic for enterohemorrhagic E. coli.

3. The method according to claim 2, wherein the oligonucleotide primer pair that hybridizes to the gene encoding heat labile toxin characteristic for enterotoxigenic E. coli is
  LT-I: 5'GCG TTA CTA TCC TCT CTA TGT G 3' (SEQ ID NO: 1) and LT-2: 5'AGT TTT CCA TAC TGA TTG CCG C 3' (SEQ ID NO: 2); and the oligonucleotide primer pair that hybridizes to the gene encoding heat stabile toxin characteristic for enterotoxigenic E. coli is
  ST-1: 5'TCC CTC AGG ATG CTA AAC CAG 3' (SEQ ID NO: 3) and ST-2a:5'TCG ATT TAT TCA ACA AAG CAA C 3' (SEQ ID NO: 4); and the oligonucleotide primer pair that hybridizes to the gene encoding heat stabile toxin characteristic for enteroaggregative E. coli is
  EASTI-1: 5'AAC TGC TGG GTA TGT GGC TGG 3' (SEQ ID NO: 5) and EASTI-2: 5'TGC TGA CCT GCC TCT TCC ATG 3' (SEQ ID NO: 6); and the oligonucleotide primer pair which hybridizes to the pCVD432 plasmid is
  EA-1: 5'CTG GCG AAA GAC TGT ATC ATT G 3' (SEQ ID NO: 7) and EA-2: 5'TAA TGT ATA GAA ATC CGC TGT T 3' (SEQ ID NO: 8); and the oligonucleotide primer pair which hybridizes to the EAF plasmid is
  EP-1: 5'CAG GGT AAA AGA AAG ATG ATA AG 3' (SEQ. ID NO: 11) and EP-2:5'AAT ATG GGG ACC ATG TAT TAT C 3' (SEQ ID NO: 12); and the oligonucleotide primer pair which hybridizes to the eae gene is
  EPeh-1: 5'CCC GCA CCC GGC ACA AGC ATA AG 3' (SEQ ID NO: 13) and EPeh-2: 5'AGT CTC GCC AGT ATT CGC CAC C 3' (SEQ ID NO: 14); and the oligonucleotide primer pair which hybridizes to the gene encoding shiga-like toxin SltI is
  SltI-1: 5'ATG AAA AAA ACA TTA TTA ATA GC 3' (SEQ ID NO: 15) and SltI-2: 5'TCA CYG AGC TAT TCT GAG TCA AGC 3' (SEQ ID NO: 16); and the oligonucleotide primer pair which hybridizes to the gene encoding shiga-like toxin SltII is
  SltII-1: 5'ATG AAG AAG ATR WTT RTD GCR CYT TTA TTY G3' (SEQ ID NO:17) and SltII-2: 5'TCA GTC ATW ATT AAA CTK CAC YTS RGC AAA KCC 3' (SEQ ID NO: 18), wherein W is AT, R is A/G, D is A/G/T, Y is C/T and K is G/T.

4. The method according to claim, wherein detecting the presence of at least one amplified product is performed using at least one oligonucleotide probe capable of hybridizing to the amplified product wherein said oligonucleotide probe is labeled at the 5'end with a fluorescent reporter dye and at the 3' end with a fluorescent quencher dye and is susceptible to 5'-3' exonuclease degradation by a polymerase, and wherein said amplification process uses a polymerase having 5'-3' exonuclease degradation activity.

5. The method according to claim 4 wherein the labeled oligonucleotide probe is selected from the group consisting of:
- a labeled oligonucleotide probe specific for the detection of a heat labile toxin gene characteristic for enterotoxigenic E. Coli;
- a labeled oligonucleotide probe specific for the detection of a heat stabile toxin gene characteristic for enterotoxigenic E. Coli;
- a labeled oligonucleotide probe specific for the detection of a heat stabile toxin gene characteristic for enteroaggregative E. Coli;
- a labeled oligonucleotide probe specific for the detection of a pCVD432 plasmid;
- a labeled oligonucleotide probe specific for the detection of an inv plasmid;
- a labeled oligonucleotide probe specific for the detection of a EAF-plasmid;
- a labeled oligonucleotide probe specific for the detection of a eae gene;
- a labeled oligonucleotide probe specific for the detection of a shiga-like toxin SltI gene; and
- a labeled oligonucleotide probe specific for the detection of a shiga-like toxin SltII gene.

6. The method according to claim 5, wherein the labeled oligonucleotide probe for the detection of heat labile toxin gene characteristic for enterotoxigenic E. coli is

5'AGC TCC CCA GTC TAT TAC AGA ACT ATG 3' (SEQ ID NO: 19), the labeled oligonucleotide probe for the detection of heat stabile toxin gene characteristic for enterotoxigenic E. coli is

5'ACA TAC GTT ACA GAC ATA ATC AGA ATC AG 3' (SEQ ID NO: 20);

the labeled oligonucleotide probe for the detection of heat stabile toxin gene characteristic for enteroaggregative E. coli is

5'ATG AAG GGG CGA AGT TCT GGC TCA ATG TGC 3' (SEQ ID NO: 21);

the labeled oligonucleotide probe for the detection of pCVD432 plasmid is

3' CTC TTT TAA CTT ATG ATA TGT AAT GTC TGG 3' (SEQ ID NO: 22);

the labeled oligonucleotide probe for the detection of the inv-plasmid is

5'CAA AAA CAG AAG AAC CTA TGT CTA CCT 3' (SEQ ID NO: 23)

the labeled oligonucleotide probe for the detection of the EAF-plasmid is

5'CTT GGA GTG ATC GAA CGG GAT CCA AAT 3' (SEQ ID NO: 24);

the labeled oligonucleotide probe for the detection of the eae gene is

5'TAA ACG GGT ATT ATC AAC AGA AAA ATC C 3' (SEQ ID NO: 25);

the labeled oligonucleotide probe for the detection of shiga-like toxin SltI gene is

5'TCG CTG AAT CCC CCT CCA TTA TGA CAG GCA 3' (SEQ ID NO: 26);

and the labeled oligonucleotide probe for the detection of shiga-like toxin SltII gene is

5'CAG GTA CTG GAT TTG ATT GTG ACA GTC ATT 3' (SEQ ID NO: 27).

7. The method according to claim 4, wherein the fluorescent reporter dye is 6-carboxy-fluorescein, tetrachloro-6-carboxy-fluorescein, or hexachloro-6-carboxy-fluorescein, and the fluorescent quencher dye is 6-carboxytetramethyl-rhodamine.

8. The method according to claim 1 wherein the amplification process comprises 35 PCR cycles at a $MgCl_2$ concentration of 5.2 mM, an annealing temperature of 55° C. and an extension temperature of 65° C.

9. A set of oligonucleotide primer pairs useful for polymerase chain reaction (PCR) amplification of pathogenic enterobacteria allowing detection and differentiation of pathogenic enterobacteria in a sample wherein following amplification the presence of at least one amplified product indicates the presence of at least one pathogenic enterobacteria strain in said sample, wherein said set comprises at least five primer pairs, wherein each primer pair specifically amplifies a DNA sequence of a virulence factor/toxin gene characteristic for one each of the subgroups of the pathogenic E. coli strains, said subgroups comprising enterotoxigenic, enteroaggregative, enteroinvasive, enteropathogenic and enterohemorrhagic E. coli strains and wherein for amplification of each subgroup at least one oligonucleotide primer pair is included in said set of oligonucleotide primer pairs, and wherein the set comprises a primer pair that hybridizes to an inv-plasmid of enteroinvasive E. coli and wherein said primer pair is El-1: 5'TTT CTG GAT GGT ATG GTG AGG 3' (SEQ ID NO: 9) and E1-2: 5'CTT GAA CAT AAG GAA ATA AAC 3' (SEQ ID NO: 10).

10. The set of primer pairs according to claim 9 comprising
- a primer pair that hybridizes to a gene encoding heat labile toxin, or to a gene encoding heat stabile toxin of enterotoxigenic E. coli;
- a primer pair that hybridizes to a gene encoding heat stabile toxin or to a pCVD432 plasmid of enteroaggregative E. coli;
- a primer pair that hybridizes to a EAF plasmid, or a eae gene of enteropathogenic E. coli; and
- a primer pair that hybridizes to a gene encoding shiga-like toxin sltl or sltII of enterohemorrhagic E. coli.

11. The set of primer pairs according to claim 10 wherein the primer pair which hybridizes to the gene encoding heat labile toxin of enterotoxigenic E. coli is LT-1: 5'GCG TTA CTA TCC TCT CTA TGT G 3' (SEQ ID NO: 1) and

LT-2: 5'AGT TTT CCA TAC TGA TTG CCG C 3' (SEQ ID NO: 2);

the primer pair which hybridizes to the gene encoding heat stabile toxin of enterotoxigenic E. coli is ST-1: 5'TCC CTC AGG ATG CTA AAC CAG 3' (SEQ ID NO: 3) and ST-2a: 5'TCG ATT TAT TCA ACA AAG CAA C 3' (SEQ ID NO: 4);

the primer pair which hybridizes to the gene encoding heat stabile toxin of enteroaggregative E. coli is EASTI-1: 5'AAC TGC TGG GTA TGT GGC TGG 3' (SEQ ID NO: 5) and

EASTI-2: 5'TGC TGA CCT GCC TCT TCC ATG 3' (SEQ ID NO: 6);

the primer pair which hybridizes to the pCVD432 plasmid is

EA-1: 5'CTG GCG AAA GAC TGT ATC ATT G 3' (SEQ ID NO: 7) and

EA-2: 5'TAA TGT ATA GAA ATC CGC TGT T3' (SEQ ID NO:8);

the primer pair which hybridizes to the EAF plasmid is

EP-1: 5'CAG GGT AAA AGA AAG ATG ATA AG 3' (SEQ ID NO: 11) and

EP-2: 5'AAT ATG GGG ACC ATG TAT TAT C 3' (SEQ ID NO: 12);

the primer pair which hybridizes to the eae gene is

EPeh-1: 5'CCC GGA CCC GGC ACA AGC ATA AG 3' (SEQ ID NO: 13) and

EPeh-2: 5'AGT CTC GCC AGT ATT CGC CAC C 3' (SEQ ID NO: 14);

the primer pair which hybridizes to the shiga-like toxin sltI gene is

SltI-1: 5'ATG AAA AAA ACA TTA TTA ATA GC 3' (SEQ ID NO: 15) and

SltI-2; 5'TCA CYG AGC TAT TCT GAG TCA AGC 3' (SEQ ID NO: 16); and the primer pair which hybridizes to the shiga-like toxin sltII is SltII-1: 5'ATG AAG AAG ATR WTT RTD GCR GYT TTA TTY G 3' (SEQ ID NO: 17) and SltII-2: 5'TCA GTC ATW ATT AAA CTK CAC YTS RGC AAA KCC 3' (SEQ ID NO: 18)

wherein W is A/T, R is A/G, D is A/G/T, Y is C/T and K is G/T.

12. A set of oligonucleotide primer pairs an a set of oligonucleotide primer probes useful for diagnosing an enterobacteria infection in samples derived from a living animal body including a human, by real time PCR method, wherein said sets of oligonucleotide primer pairs and oligonucleotide probes allow detection and differentiation of pathogenic enterobacteria in a sample, wherein said set of oligonucleotide primer pairs comprises at least five primer pairs, wherein each primer pair specifically amplifies a DNA sequence of a virulence factor/toxin gene characteristic for one each of the subgroups of the pathogenic *E. coli* strains, said subgroups comprising enterotoxigenic, enteroaggregative, enteroinvasive, enteropathogenic and enterohemorrhagic *E. coli* strains and wherein for amplification of each subgroup at least one oligonucleotide primer pair is included in said set of oligonucleotide primer pairs, and wherein the set comprises a primer pair that hybridizes to an inv-plasmid of enteroinvasive *E. coli*, wherein said primer pair is El-1: 5ΔTTT CTG GAT GGT ATG GTG AGG 3' (SEQ ID NO: 9) and E1-2: 5'CTT GAA CAT AAG GAA ATA AAC 3' (SEQ ID NO: 10).

13. The method of claim 1, wherein said method is used to diagnose an enterobacteria infection in a sample derived from a living animal body.

14. The method of claim 13, wherein said sample is derived from a human.

15. The method of claim 1, wherein said method is used to detect enterobacteria contamination of a consumable.

16. The method of claim 15, wherein said consumable is selected from the group consisting of meat, milk and vegetable.

* * * * *